(12) United States Patent
Kaufman

(10) Patent No.: US 11,707,436 B2
(45) Date of Patent: Jul. 25, 2023

(54) METHODS OF TREATING INFLAMMATORY DISORDERS AND GLOBAL INFLAMMATION WITH COMPOSITIONS COMPRISING PHOSPHOLIPID NANOPARTICLE ENCAPSULATIONS OF NSAIDS

(71) Applicant: NanoSphere Health Sciences, LLC, Greenwood Village, CO (US)

(72) Inventor: Richard Clark Kaufman, Santa Monica, CA (US)

(73) Assignee: NANOSPHERE HEALTH SCIENCES INC.

(*) Notice: Subject to any disclaimer, the term of this patent is extended or adjusted under 35 U.S.C. 154(b) by 0 days.

(21) Appl. No.: 15/536,134

(22) PCT Filed: Dec. 14, 2015

(86) PCT No.: PCT/US2015/065611
§ 371 (c)(1),
(2) Date: Jun. 15, 2017

(87) PCT Pub. No.: WO2016/100228
PCT Pub. Date: Jun. 23, 2016

(65) Prior Publication Data
US 2018/0055782 A1    Mar. 1, 2018

Related U.S. Application Data

(60) Provisional application No. 62/091,994, filed on Dec. 15, 2014.

(51) Int. Cl.
| A61K 9/51 | (2006.01) |
| A61K 9/00 | (2006.01) |
| A61K 31/616 | (2006.01) |
| A61K 31/192 | (2006.01) |

(52) U.S. Cl.
CPC ............ *A61K 9/5123* (2013.01); *A61K 9/006* (2013.01); *A61K 9/0014* (2013.01); *A61K 9/0048* (2013.01); *A61K 31/192* (2013.01); *A61K 31/616* (2013.01)

(58) Field of Classification Search
CPC .................................................. A61K 9/5123
See application file for complete search history.

(56) References Cited

U.S. PATENT DOCUMENTS

| 3,380,826 A * | 4/1968 | Deary ................... H01J 9/2271 430/28 |
| 5,662,932 A * | 9/1997 | Amselem ............. A61K 9/5123 424/490 |
| 5,716,637 A | 2/1998 | Anselem et al. |
| 5,744,155 A * | 4/1998 | Friedman ............. A61K 9/0048 424/434 |
| 6,004,566 A * | 12/1999 | Friedman ............... A61Q 19/00 424/400 |
| 9,925,149 B2 | 3/2018 | Kaufman |
| 10,028,919 B2 | 7/2018 | Kaufman |
| 2003/0096000 A1 | 5/2003 | Solis et al. |
| 2005/0266067 A1 | 12/2005 | Sengupta et al. |
| 2008/0113031 A1 | 5/2008 | Moodley et al. |
| 2008/0311214 A1* | 12/2008 | Rao ..................... A61K 9/0019 514/1.1 |
| 2009/0074824 A1 | 3/2009 | Vila Pena et al. |
| 2011/0071118 A1 | 3/2011 | Lichtenberger |
| 2011/0312910 A1 | 12/2011 | Dikovskiy et al. |
| 2012/0093931 A9 | 4/2012 | McGinnis et al. |
| 2012/0321670 A1 | 12/2012 | Doshi et al. |
| 2013/0095032 A1 | 4/2013 | Margalit et al. |
| 2014/0328759 A1 | 11/2014 | Cullis et al. |
| 2014/0348926 A1 | 11/2014 | Hoffman et al. |
| 2015/0231070 A1* | 8/2015 | Huang ................... A61K 38/13 424/400 |
| 2016/0263047 A1 | 9/2016 | Kaufman |
| 2017/0000744 A1 | 1/2017 | Kaufman |
| 2018/0296493 A1 | 10/2018 | Kaufman et al. |

FOREIGN PATENT DOCUMENTS

| EP | 0249561 A2 * | 12/1987 | ............... A61K 9/50 |
| EP | 3057604 | 8/2016 | |
| EP | 3268043 | 1/2018 | |
| WO | 1993/05768 | 4/1993 | |
| WO | WO-9305768 A1 * | 4/1993 | ........... A61K 9/1617 |
| WO | WO-9733562 A1 * | 9/1997 | ........... A61K 9/0048 |
| WO | 2001/049268 | 7/2001 | |
| WO | WO 2008/010788 | 1/2008 | |
| WO | 2008/019146 | 2/2008 | |
| WO | WO 2010/008762 | 1/2010 | |
| WO | WO 2012/066334 A1 | 5/2012 | |
| WO | WO 2012/003003 A2 | 10/2012 | |

(Continued)

OTHER PUBLICATIONS

Google Patents English Translation of WO 9305768 A1. Obtained from https://patents.google.com/patent/WO1993005768A1/en?oq=surfactant+free+sln on Jul. 26, 2018. 14 printed pages. Document originally published in German on Apr. 1, 1993. (Year: 1993).*

(Continued)

*Primary Examiner* — Isaac Shomer
(74) *Attorney, Agent, or Firm* — Adsero IP

(57) ABSTRACT

Novel process and products thereby emplace NSAIDS within nanodelivery vehicles for various indications in mammals, including humans.

2 Claims, No Drawings

(56) References Cited

FOREIGN PATENT DOCUMENTS

| WO | WO 2013/105101 A1 | 7/2013 |
|----|-------------------|--------|
| WO | 2015/057751 | 4/2015 |
| WO | WO 2015/057751 A1 | 4/2015 |
| WO | 2015/068052 | 5/2015 |
| WO | 2016/100228 | 6/2016 |
| WO | WO 2016/100228 | 6/2016 |
| WO | 2016/144376 | 9/2016 |
| WO | WO 2016/144376 | 9/2016 |

OTHER PUBLICATIONS

ML Bondi, R Di Gesu, EF Craparo. "Lipid Nanoparticles for Drug Targeting to the Brain." Methods in Enzymology, vol. 508, 2012, pp. 229-251. (Year: 2012).*
A Mistry, S Stolnik, L Illum. "Nanoparticles for direct nose-to-brain delivery of drugs." International Journal of Pharmaceutics, vol. 379, 2009, pp. 146-157. (Year: 2009).*
Abstract of TK Vyas, A Shahiwala, S Marathe, A Mistra. "Intranasal drug delivery for brain targeting." Pubmed ID: 16305417. Obtained from https://www.ncbi.nlm.nih.gov/pubmed/16305417 on Jul. 26, 2018. 1 printed page. Original article published in 2005. (Year: 2005).*
Lipoid, www.lipoid.com/en/node/105 accessed Aug. 16, 2019, 1 printed page. (Year: 2019).*
W Mehnert, K Mader. "Solid lipid nanoparticles Production, characterization and applications." Advanced Drug Delivery Reviews, vol. 47, 2001, pp. 165-196. (Year: 2001).*
Ganjly. https://www.ganjly.com/dr-richard-kaufman-interview-chief-science-officer-of-nanosphere-health-sciences/ accessed Feb. 16, 2021, pp. 1-6. (Year: 2021).*
Lauren M. Posnick, Henry Kim, Catherine "Kitty" Bailey. "Bottled Water Regulation and the FDA." Reproduced from Food Safety Magazine, Aug./Sep. 2002, with permission of the publisher, 4 printed pages. (Year: 2002).*
FDA CFR—Code of Federal Regulations Title 21. https://www.accessdata.fda.gov/scripts/cdrh/cfdocs/cfcfr/CFRSearch.cfm?fr=182.1320&SearchTerm=glycerin accessed Aug. 25, 2021, 2 printed pages. (Year: 2021).*
Anthony A. Attama, Stephan Reichl Christel C. Müller-Goymann. "Diclofenac sodium delivery to the eye: In vitro evaluation of novel solid lipid nanoparticle formulation using human cornea construct." International Journal of Pharmaceutics 355 (2008) 307-313. (Year: 2008).*
Yan Liu, Xia Lin and Xing Tang. "Lipid emulsions as a potential delivery system for ocular use of azithromycin." Drug Development and Industrial Pharmacy, 2009; 35(7): 887-896. (Year: 2009).*
Dragomir Kompan and Andreja Komprej. "The Effect of Fatty Acids in Goat Milk on Health." https://www.intechopen.com/chapters/39464 accessed Feb. 2, 2022, originally published Sep. 26, 2012, pp. 1-31. (Year: 2012).*
A.C. Silva, D. Santos, D. Ferreira and C.M. Lopes. "Lipid-based Nanocarriers as an Alternative for Oral Delivery of Poorly Water-Soluble Drugs: Peroral and Mucosal Routes." Current Medicinal Chemistry, vol. 19, 2012, pp. 4495-4510. (Year: 2012).*
Eliana B. Souto et al. "Feasibility of Lipid Nanoparticles for Ocular Delivery of Anti-Inflammatory Drugs." Current Eye Research, vol. 35(7), 2010, pp. 537-552. (Year: 2010).*
Roberta Cavalli et al. "Solid lipid nanoparticles (SLN) as ocular delivery system for tobramycin." International Journal of Pharmaceutics, vol. 238, 2002, pp. 241-245. (Year: 2002).*
A. A. Attama et al. "Sustained Release and Permeation of Timolol from Surface-Modified Solid Lipid Nanoparticles through Bioengineered Human Cornea." Current Eye Research, vol. 34, 2009, pp. 698-705. (Year: 2009).*
Tushar K. Vyas, Aliasgar Shahiwalak Sundhavna Marathe, and Ambikanadan Mistra. "Intranasal Drug Delivery for Brain Targeting." Current Drug Delivery, vol. 2, 2005, pp. 165-175. (Year: 2005).*
International Preliminary Report on Patentability for PCT/US2015/065611, dated Jun. 29, 2017, 7 pages.
International Search Report for PCT/US2015/065611, dated Jun. 30, 2016, 21 pages.
Kaufman, Nanosphere Delivery Systems, Life Enhancement Products, Aug. 2013 [retrieved on Feb. 4, 2016], pp. 1-8, Retrieved from the internet: URL: http://www.life-enhancement.com/magazine/article/2910-nanosphere-delivery-systems.
Bondi et al., "Lipid Nanoparticles for Drug Targeting to the Brain", Methods in Enzymology, vol. 508, pp. 229-251.
English translation of WO 93057686—google translation—obtained from https://patents.google.com/patent/WO1993005768A1/en?og=surfactant+free+sin on Jul. 26, 2018.
Full Examination Report for Application No. 2015385825, dated Mar. 15, 2018, 3 pages.
Mistry et al., "Nanoparticles for direct nose-tobrain delivery of drugs", International Journal of Pharmacuetics 379 (2009) 146-157.
Office Action for Application No. 2,970,917, dated Apr. 25, 2018, 4 pages.
Office Action for Application No. 2,979,184, dated Oct. 12, 2018, 4 pages.
Vyas et al., "Intranasal drug delivery forbrain targetring", Curr Drug Deliv, Apr. 2, 2005(2): 165-175, obtained from https://www.ncbi.nlm.nih.gov/pubmed/16305417 on Jul. 26, 2018. Abstract.
Chaturvedi et al., "Research Journal of Pharmaceutical, Biological and Chemical Sciences", Jul.-Sep. 2012, RJPBCS, vol. 3, Issue 3: 525-541.
Communication pursuant to Article 94(3) EPC for Application No. 14854788.8, dated May 13, 2019, 8 pages.
Das et al., "Recent Advances in Lipid Nanoparticle Formulations with Solid Matrix for Oral Drug Delivery", AAPS PharmSciTech, vol. 12, No. 1, Mar. 2011: 62-76.
Ekambaram et al., "Solid Lipid Nanoparticles: A Review", Sci. Revs. Chem. Communl: 2(1), 2012: 80-102.
Extended EP Search Report for Application 158849894.5, dated Nov. 16, 2018, 10 pages.
Tran et al., "Solid Lipid Nanoparticles for Poorly Water-Soluble Drugs", 2016, JSM Nanotechnol. .Nanomed. 4(1): 1038, pp. 1-5.

* cited by examiner

METHODS OF TREATING INFLAMMATORY DISORDERS AND GLOBAL INFLAMMATION WITH COMPOSITIONS COMPRISING PHOSPHOLIPID NANOPARTICLE ENCAPSULATIONS OF NSAIDS

CROSS-REFERENCE TO RELATED APPLICATIONS

This application is a 35 U.S.C. § 371 national phase application of PCT/US2015/065611 (WO 2016/100228) filed on Dec. 14, 2015, entitled " Methods of Treating Inflammatory Disorders and Global Inflammation with Compositions Comprising Phospholipid Nanoparticle Encapsulations of NSAIDS ", which application claims the priority benefit of U.S. Provisional Application No. 62/091,994, filed Dec. 15, 2014, and entitled "Methods of Treating Inflammatory Disorders and Global Inflammation with Compositions Comprising Phospholipid Nanoparticle Encapsulations of NSAIDs", which are incorporated herein by reference in their entirety.

TECHNICAL FIELD

This disclosure teaches phospholipid nanoparticle compositions of NSAIDs (non-steroidal anti-inflammatory drugs) formed from phospholipids and simpler lipids in an unfired sequential process that encapsulate a high concentration of NSAIDs; yielding an increase NSAID transport across hydrophobic mucosa; increase the bioavailability of the NSAID 2-fold to 10-fold, decrease the dose of NSAIDs 2-fold to 10-fold less than an amount of NSAID needed to illicit the same therapeutic effect compared to standard NSAID pills and capsules currently sold; where the phospholipids in the nanoparticle structure reduce or eliminate pathogenic effects of NSAIDs; and enable safe, daily, long term and more efficacious NSAID therapy and treatment and prevention of inflammatory disorders and global inflammation.

BACKGROUND

OTC (over-the-counter) and prescription NSAIDs are primarily sold as solid dose forms compressed into pills and filled into capsules. Nearly half the population has a hard time swallowing pills and capsules. A recent Harris poll reported individuals find swallowing pills so difficult that many delay, skip, or discontinue taking the pills or capsules completely. To facilitate swallowing, they mostly drink lots of liquids, drink in big gulps or tilt their heads back. People having problems taking pills described the sensations as having a pill stuck in their throat, a bad after taste or gagging.

NSAIDs can produce adverse effects that are a concern to long-term treatments and high dose usage. The most common adverse effects of NSAIDs are platelet dysfunction, gastritis and peptic ulceration with bleeding, acute renal failure in susceptible, sodium & water retention, edema, analgesic nephropathy, hypersensitivity due to PG (prostaglandin) inhibition and GI bleeding and perforation Everyone who takes NSAIDs is at some risk for developing a stomach problem for their regular use in treating aging. NSAIDs can cause gastrointestinal (GI) problems from mild stomach upset and pain to serious stomach bleeding and ulcers or perforation of the GI mucosal lining, a factor that limits their use. The major concern with the chronic usage of NSAIDs is that 30 to 40% of patients using NSAIDs have a GI intolerance to the drugs and suffer from a spectrum of symptoms Recent studies indicate that NSAIDs may increase the chance of heart attack or stroke An authoritative new analysis of more than 350,000 patients, concludes that people who take high doses of NSAIDs daily increase their cardiovascular risk by as much as a third, compared with those taking a placebo. The exception is naproxen (and low dose aspirin), which may actually have a protective effect against heart attacks. NSAIDs are also associated with a relatively high incidence of renal adverse drug reactions. Daily use and high dosages of NSAIDs can block the kidney's defense mechanisms and makes any other form of kidney injury worse. There is also a low risk of liver damage from NSAID therapy.

Despite the extensive work in the area of NSAIDs, and delivery systems, a need exists in the art for methods and compositions of NSAIDs to overcome their intrinsic low solubility and dissolution, reduce NSAID dosages without loss of therapeutic efficacy, are suitable for long-term or daily NSAID therapy and don't produce toxic or adverse effects.

There also continues to exist in the art the need for more effective delivery systems of NSAIDs that target and block transcriptional inflammatory pathways, pro-inflammatory cytokines and mediators of inflammation from causing pathology.

There also continues to exist in the art for methods and delivery system compositions of NSAIDs that increase the bioavailability, bioactivity, therapeutic activity and therapeutic index of NSAIDs for NSAID therapy and for use in the treatment and prevention or inflammatory disorders and global inflammation.

Methods and compositions that provide enhanced NSAID anti-inflammatory bioactivity, increased therapeutic activity, site specific targeting, and at lower doses; and administered by more effective, methods of delivery than the problematic swallowing of pills and capsules currently prescribed for pharmacological activity, would make NSAID drugs available to those previously unable to tolerate standard and/or prolonged therapeutic regimens of NSAIDs.

SUMMARY OF THE EMBODIMENTS

This disclosure teaches phospholipid nanoparticle compositions of NSAIDs formed from phospholipids and simpler lipids in an unfired sequential process that encapsulate a high concentration of NSAIDs; yielding an increase NSAID transport across hydrophobic mucosa; increase the bioavailability of the NSAID 2-fold to 10-fold, decrease the dose of NSAIDs 2-fold to 10-fold less than an amount of NSAID needed to illicit the same therapeutic effect compared to standard NSAID pills and capsules currently sold; where the phospholipids in the nanoparticle structure reduce or eliminate pathogenic effects of NSAIDs; and enable safe, daily, long term and more efficacious NSAID therapy and treatment and prevention of inflammatory disorders and global inflammation.

The present disclosure also teaches phospholipid NSAID compositions for treating fever, inflamed tissues, platelet aggregation, and/or central and/or peripheral or nervous system disorders; and/or preventing thrombosis; and in a therapeutic dose 2-fold to 10-fold less than the typical dose of currently sold NSAID pills and capsules; and without causing NSAID pathogenic effects.

The disclosure teaches the use of phospholipid nanoparticle compositions encapsulating NSAIDs enabling NSAIDs to efficiently pass the blood brain barrier and enter the central nervous to block inflammation and inflammatory pathways and mediators of inflammation in neural structures that are recognized to initiate neurodegenerative disorders and systemic aging.

The disclosure teaches the use of phospholipid nanoparticle compositions encapsulating anti-inflammatory nutraceuticals including resveratrol, cinnamaldehyde, green tea polyphenols, lipoic acid, and curcuminoids to efficiently pass the blood brain barrier and enter the central nervous to block inflammation and inflammatory pathways and mediators of inflammation in neural structures that are recognized to initiate neurodegenerative disorders and systemic aging.

The disclosure teaches the use of phospholipid nanoparticle compositions encapsulating anti-inflammatory Cannabidiol to efficiently pass the blood brain barrier and enter the central nervous to block inflammation and inflammatory pathways and mediators of inflammation in neural structures that are recognized to initiate neurodegenerative disorders and systemic aging.

The disclosure teaches encapsulating NSAIDs in NanoSpheres and phospholipid nanoparticles increase the bioavailability and bioactivity of NSAIDs to effectively target and block NF-kappaB activation, proinflammatory cytokines and mediators of inflammation that create global inflammatory responses and inflammatory disease pathology; and increases the therapeutic activity of NSAIDs in NSAID therapy and for inflammatory disorders that include and are not limited to conditions that include diabetes, cancer, arthritis, pain, heart disease, osteoporosis, neurodegeneration, dementia, obesity and depression.

This disclosure teaches encapsulating NSAIDs in phospholipid nanoparticles liquid gels enabling NSAIDs to be taken by sublingual intraoral, peroral, nasal and transdermal routes of administration and produce greater therapeutic acclivity with a higher therapeutic index compared to the commercial forms and similar doses of the same NSAID taken by peroral administration.

This disclosure teaches the phospholipid nanoparticles encapsulation of anti-inflammatory nutraceuticals including resveratrol, cinnamaldehyde, green tea polyphenols, lipoic acid, and curcuminoids to block NF-KappaB activation, inhibit pro-inflammatory pathways and mediators of inflammation; increase their bioavailability, bioactivity and therapeutic activity; and prevent, ameliorator or treat inflammatory disorders and/or global inflammation.

This disclosure teaches the phospholipid nanoparticles encapsulation of anti-inflammatory cannabididiol to block NF-KappaB activation, inhibit pro-inflammatory pathways and mediators of inflammation; increase their bioavailability, bioactivity and therapeutic activity; and prevent, ameliorator or treat inflammatory disorders and/or global inflammation. This disclosure teaches phospholipid nanoparticles encapsulation of antioxidants such as N-acetylCysteine and Glutathione to inhibit oxidative stress; block NF-KappaB activation, inhibit pro-inflammatory pathways and mediators of inflammation; increase their bioavailability, bioactivity and therapeutic activity; and prevent, ameliorator or treat inflammatory disorders and/or global inflammation.

This disclosure teaches phospholipid nanoparticles encapsulation of protease inhibitors, antisense oligodeoxynucleotides to block NF-KappaB activation, inhibit pro-inflammatory pathways and mediators of inflammation; increase their bioavailability, bioactivity and therapeutic activity; and prevent, ameliorator or treat inflammatory disorders and/or global inflammation.

The disclosure teaches the method of treating a patient in need of anti-inflammation therapy comprising treatment with phospholipid nanoparticle composition of NSAIDs formed from phospholipids and simpler lipids in an unfired sequential process that encapsulate a high concentration of NSAIDs.

The disclosure teaches the method of treating a patient comprising treatment with phospholipid nanoparticle composition of NSAIDs formed from phospholipids and simpler lipids in an unfired sequential process that encapsulate a high concentration of NSAIDs.

This disclosure teaches methods of phospholipid nanoparticle carrier compositions of NSAIDS direct nose-to-brain drug delivery into CNS (Central Nervous System) via the intranasal route of administration that bypass the BBB (Blood Brain Barrier), and increase the therapeutic activity of NSAIDs to treat inflammatory disorders, neurodegenerative conditions and global inflammation in the CNS; and bypass the GI (Gastrointestinal) tract to prevent NSAID pathogenic effects.

This disclosure teaches methods of phospholipid nanoparticle carrier compositions of NSAIDS delivery across the BBB, and increase the therapeutic activity of NSAIDs to treat inflammatory disorders, neurodegenerative conditions and global inflammation in the CNS; and reduce or eliminate NSAID pathogenic effects.

This disclosure teaches methods of treatment for a patient comprising phospholipid nanoparticle carrier compositions of NSAIDS delivery.

DETAILED DESCRIPTION OF THE DISCLOSURE

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The term "phospholipid nanoparticle" in the present disclosure refers to different types of compositions of nanoscale particles as carriers containing essential phospholipids that encapsulate NSAIDs by using a molecular assembly technique to carry the NSAID across cell membranes and biological barriers to deliver the NSAID to target cell sites of the human body where they are released to block inflammation and produce therapeutic activity.

The term "NanoSpheres" in the present disclosure refer to phospholipid lipid nanoparticles as liquid gels that are mostly less than 100 nm diameter and typically in the range of 50 nm to 150 nm. NanoSpheres have high stability and minimal leakage of contents into the GI tract and blood. NanoSpheres possess high long-term stability. Nanospheres allow for high encapsulation of NSAIDs, and strong protection of ingredients. Nanospheres have a high degree of compatibility, versatility usability and safety for NSAIDs.

The term "phospholipids" in the present disclosure refer to a triester of glycerol with two fatty acids and one phosphate ion. They include natural occurring phospholipids like phophatdylchline sphingosine, gangliosides, and phytosphingosine and combinations thereof derived from soy and lecithin that are preferable for use in this disclosure and the synthetic phospholipids that include but are not limited to diacylglycerols, phosphatidic acids, phosphocholines, phosphoethanolamines, phosphoglycerols, The term "essential phospholipids" in the present disclosure refers to the highly purified extract of characteristic fatty acid composition of the phospholipids distinguished by their particular high content of polyunsaturated fatty acids, predominantly linoleic acid (approx. 70%), linolenic acid and olelc acid and with a high content exceeding 75% of (3-sn-phosphatidyl) choline. Beside phosphatidylcholine molecules, the essential phospholipid fraction includes phosphatidylethanolamine, phosphatidylinosit and other lipids.

The term "medium chain triglyceride" (MCT) "in the present disclosure refer a class of triglyceride oil that are probably naturally derived from fatty acids that are usually about 8 to about 12 carbons in length. Such oil is commercially available as Miglyol 812, Miglyol 810, Captex 355 and Neobees M-5

The term "NSAID" in this disclosure refers to any of the following non-steroidal anti-inflammatory drugs that inhibits cyclooxygenases: Propionic acid drugs such as Fenoprofen calcium (Nalfon®), Flurbiprofen (Ansaid®), Suprofen. Benoxaprofen, Ibuprofen (prescription Motrin®), Ibuprofen (200 mg. over the counter Nuprin, Motrin 1B®), Ketoprofen (Orduis, Oruvall®), Naproxen (Naprosyn®), Naproxen sodium (Aleve, Anaprox, Aflaxen®), Oxaprozin (Daypro®), or the like; Acetic acid drug such as Diclofenac sodium (Voltaren®), Diclofenac potassium (Cataflam®), Etodolac (Lodine®), Indomethacin (Indocin®), Ketorolac tromethamine (Acular, Toradol® intramuscular), Ketorolac (oral Toradol®), or the like; Ketone drugs such as Nabumetone (Relafen®), Sulindac (Clinoril®), Tolmetin sodium (Tolectin®), or the like; Fenamate drugs such as Meclofenamate sodium (Meclomen®), Mefenamic acid (Ponstel®), or the like; Oxicam drugs such as Piroxicam (Dolibid®), or the like; Salicylic acid drugs such as Diflunisal (Feldene®), Aspirin, or the like; Pyrazolin acid drugs such as Oxyphenbutazone (Tandearil®), Phenylbutazone (Butazolidin®), or COX-2 inhibitors such as celecoxib, meloxicam, diclofenac, meloxicam, piroxicam, Celebrex, Vioxx, or the like; or mixtures or combinations thereof.

The term "bioavailability"" in this disclosure refers to the pysiologic availability of a given amount of a drug, as distinct fromits chemical potency; proportion of the ad ministered dose that is absorbed into the bloodstream The term "therapeutic activity" in this disclosure refers the effect or response of a drug in the treating or curing of disease.

The term "therapeutic index" in this disclosure refers to the therapeutic window or safety window and comparison of the amount of a therapeutic agent that causes the therapeutic effect to the amount that causes toxicity.

The term "NSAID pathogenic effects" in this disclosure refer the adverse effect of "NSAID Therapy". These problems include stomach problems, GI ulceration, bleeding, liver damage, kidney damage, and/or cardiovascular side effects The term "NSAID therapy" in this disclosure refer the use of NSAIDs to prevent, and/or ameliorate acute and/or chronic inflammation; prevent, treat and/or ameliorate global inflammation; and/or prevent, treat and/or ameliorate inflammatory disorders, and/or reduce inflammation.

The term "inflammatory disorders" in this disclosure refers to any inflammatory disorder and pathology related to chronic and/or acute inflammation; and disorders related to activation of the NF-κB signaling pathway and the actions of pro-inflammatory cytokines, mediators of inflammation and cyclooxygenases Inflammatory disorders include Type I & II Diabetes, Insulin Resistance, Cardiovascular disease, Atherosclerosis, Vascular Disorders, Chronic Heart Failure, Stroke, Cerebral Aneurism, Neurodegenerative Disorders including Parkinsonism and ALS Dementia, (both vascular and Alzheimer's types), Cognitive Decline, Cancer, Tumor Formation, Rheumatoid Arthritis, Osteoarthritis, Systemic lupus erythematous, GI Tract Problems, Inflammatory Bowel Disorders, Metabolic Obesity, Hepatic inflammation and fibrosis, Sarcopenia age-related loss of muscle mass, strength and function, Anorexia of aging, Allergies. Sinusitis, Anxiety Disorders, Depression, Osteoporosis age-associated low bone mass condition, Pulmonary Disease, Pulmonary Hypertension, COPD, Kidney Disease, Glomular Disease, Skin Disease, Neuropathic and Inflammatory Pain and Migraine Headaches.

The term "global inflammation" in this disclosure refers to low-grade, systemic, unresolved and molecular inflammation. Global inflammation is described as a hallmark of aging, and an underlying mechanism of aging and related to pathological processes of the individual age-related inflammatory diseases.

The term "NSAID pathogenic effects" in this disclosure refer to the adverse effect of "NSAID Therapy". These problems include irritation of the epidermis, stomach problems, GI ulceration, bleeding, liver damage, kidney damage, and/or cardiovascular side effects.

The terms "cell membranes", "biological barriers" and "mucosa barriers" in this disclosure refer to 1) the mucosal membrane barriers of the oral cavity; 2) the mucosal membrane barrier of the GI tract; 3) the dermal and epidermal cell membrane barriers; 4) the BBB; 5) the blood-ocular barrier consisting of the blood-aqueous barrier and the blood-retinal barrier; 6) ocular barriers of the conjunctiva and corneal epithelium; and 7) the mucosa of the nasal cavity 8) the cell membrane barriers of the nervous system, respiratory system, circulatory system, GI system, muscular system, urinary system, genital system, internal organs, and tissues.

The term mammal is intended to include, but not limited to, humans in this disclosure.

Phospholipids Protection of GI Pathology from NSAIDs

Serious side effects can occur on the digestive tract such as damage to the mucous membrane or gastric ulcer formation by non-steroidal antiphlogistic substances. This disclosure teaches phospholipid nanoparticle compositions of NSAIDs formed from phospholipids and simpler lipids can prevent and or diminish these side effects. The addition of a phospholipid such as phosphatidylcholine to an NSAID has resulted in little or no GI injury after acute or chronic dosing in animals and humans. The combination of a phospholipid and an NSAID has a greater ability to relieve pain, fever, and inflammation than unmodified NSAIDs.

Phosphatidylcholine protects against gastric ulcers caused by NSAIDs given a simultaneous administration of a purified phosphatidylcholine. Phospholipids form a barrier to help prevent stomach acid from damaging the underlying epithelium.

Chronic Inflammation is Hallmark of Aging

Inflammation is a hallmark of aging that contributes to the aging process. Global studies on the transcriptional landscape of aged tissues have also emphasized the relevance of inflammatory pathways in the aging process and the diseases of aging. A prominent aging-associated alteration in intercellular communication is "inflammaging," a pro-inflammatory phenotype that accompanies aging in mammals. Inflammaging result from multiple causes, such as the accumulation of proinflammatory tissue damage, the failure of the immune system to effectively clear pathogens and dysfunctional host cells, of senescent cells secreting proinflammatory cytokines the enhanced activation of the NF-KappaB transcription factor, or the occurrence of a defective autophagy response. These alterations result in enhanced activation pro-inflammatory pathways, finally leading to increased production of IL-1β, tumor necrosis factor, and interferons and other mediators of inflammation.

An accumulating body of evidence indicates that unresolved, low-grade chronic systemic inflammation plays a significant role in modulating the aging process, and age-related diseases, such as metabolic syndrome, diabetes, sarcopenia, dementia, atherosclerosis, cancer and osteoporosis. The close involvement of inflammation in these diseases has led them to be named as "inflammatory diseases." Low-grade, unresolved, molecular inflammation is described as an underlying mechanism of aging and age-related diseases, serving as a bridge between normal aging and age-related pathological processes. Continuous (chronic) up-regulation of pro-inflammatory mediators (e.g., TNF-αlpha, IL-1beta, Il-6, cyclooxygenase 2 (COX-2) adhesion molecules, and inducible NO synthase, iNOS) are the culprits behind inflammatory disorders and induced during the aging process due to an age-related redox imbalance that are tied to and regulated by NF-kappaB signaling pathway. There is also breakdown in the well-maintained balance between NF-kappaB and the family of transcription factors, PPARs (PPARalpha, gamma) as regulators of pro-inflammatory responses in inducing inflammatory disorders.

Many studies on changes in the transcription factor NF-kappaB have consistently shown increased activity with age and in a variety of tissues, including heart, liver, kidney, and brain tissues. Studies show that chronic inflammation can accelerate aging via ROS-mediated exacerbation of telomere dysfunction and cell death.

Underlying Molecular Mechanisms of Inflammation and Aging Disorders

NF-KappaB (nuclear factor kappa-light-chain-enhancer of activated B cells) is a protein complex that reads and copies the DNA (a transcription factor). The NF-KappaB transition factor is regarded as the master regulator of inflammation. NF-kappaB controls the global pro-inflammatory response in endothelium and coordinates the global expression of various soluble pro-inflammatory mediators (e.g., cytokines and chemokines) and molecules. NF-kappaB is a transcription factor has an essential role in inflammation and innate immunity NF-KappaB regulates host inflammatory and immune responses by increasing the expression of specific cellular genes that encode least 27 different cytokines and chemokines, receptors involved in immune recognition and inflammatory processes NF-κB, the stimulates pro-inflammatory cytokines IL-1β, Il-6 and TNF-α. And these inflammatory cytokines directly activate the NF-κB pathway. This positive autoregulatory loop can amplify the inflammatory response and increase the duration of chronic inflammation.

NF-KappaB stimulates the expression of enzymes whose products contribute to the pathogenesis of the inflammatory process. This includes the inducible form of nitric oxide synthase (iNOS) that generates nitric oxide (NO), and the inducible cyclooxygenase (COX-2) that generates prostanoids The NF-κB pathway controls immune responses and regulates IL-2 production, which increases the proliferation and differentiation of T lymphocytes. It is evident that activation of NF-KappaB induces multiple genes that regulate the immune and the inflammatory response. In addition to activating the expression of genes involved in the control of the immune and inflammatory response, the NF-κB pathway is also a key mediator of genes involved in the control of the cellular proliferation and apoptosis.

NF-KappaB is classified as a "rapid-acting" transcription factor, i.e., transcription factors that are present in cells in an inactive state and do not require new protein synthesis in order to become activated. In the absence of inflammatory activity, NF-κB is retained in the cytoplasm in a resting state by a protein inhibitor IkB (part of a family of related proteins). Proinflammatory stimuli activate a specific protein kinase, resulting in the degradation of IκB and translocation of NF-KappaB into the nucleus in where it binds to specific elements (κB-sites) within the promoters of responsive genes to activate their transcription for inflammatory and immune responses.

While chronic activation of NF-KappaB and an increasing level of inflammation hallmark of aging and aging disorders, too little NF-KappaB activation leads to susceptibility to viral infection and improper immune development. In addition to pro-inflammatory cytokines (IL-1β, Il-6 and TNF-α), other activators NF-KappaB include free radicals, ultraviolet irradiation, oxidized LDL, and bacterial or viral infections, cocaine, and ionizing radiation.

Pathology from Chronic Inflammation

Many diseases are recognized as inflammatory disorders related to chronic inflammation from activation of the NF-KappaB signaling pathway and the excessive activity of pro-inflammatory cytokines and mediators of inflammation. The list includes but is not limited to:

Type I & II Diabetes, Insulin Resistance;
Cardiovascular disease, Atherosclerosis, Vascular Disorders, Chronic Heart Failure;
Stroke, Cerebral Aneurism;
Neurodegenerative Disorders including Parkinsonism and ALS;
Dementia, (both vascular and Alzheimer's types), Cognitive Decline;
Cancer, Tumor Formation;
Rheumatoid Arthritis, Osteoarthritis, Systemic lupus erythematous
GI Tract Problems, Inflammatory Bowel Disorders;
Metabolic Obesity;
Hepatic inflammation and fibrosis;
Sarcopenia age-related loss of muscle mass, strength and function;
Anorexia of aging
Allergies, Sinusitis;
Anxiety Disorders, Depression;
Osteoporosis age-associated low bone mass condition
Pulmonary Disease Pulmonary Hypertension, COPD
Kidney Disease, Glomular Disease;
Skin Disease
Neuropathic and Inflammatory Pain;
And Migraine Headaches.

This disclosure teaches the use of phospholipid nanoparticle compositions of NSAIDs formed from phospholipids as a treatment for inflammatory disorders.

Inflammation in the hypothalamus may underlie aging of the entire body from over-activation of the inflammatory proteins and pathways. Over-activation of the inflammatory protein NF-KappaB in the brain region leads to a number of aging-related changes, from cognitive decline to muscle weakness. Unexpectedly, this process promotes aging by suppressing gonadotropin-releasing hormone (GnRH), which stimulates adult neurogenesis. This decline in GnRH contributes to numerous aging-related conditions, changes such as bone fragility, muscle weakness, skin atrophy, and reduced neurogenesis.

Activation of NF-kappaB signaling pathways mediate the events in the inflammatory response by chondrocytes leading to progressive extracellular matrix damage and the destruction or articular tissue casing rheumatic disorders and arthritis conditions of aging.

The prevalence of persistent pain increases with age. Painful conditions such as fibromyalgia, chronic low back pain, osteoarthritis, and neuropathic pain are linked to the activation of the NF-kappaB inflammatory signaling pathways from aging. Italian researchers found activation of the NF-kappaB inflammatory signaling pathways were responsible for low back pain and other acute vertebral problems like cervical axial pain, and degeneration of the vertebral column all due to aging. NF-KappaB activation in nociception encoding and processing of harmful stimuli in the nervous system from specialized receptors results in the subjective feeling of pain.

The key mediators of inflammatory reactions (i.e., IL-1β, IL-6, TNF-α, COX-2, and iNOS) have all been shown to up-regulate during the aging process from the activation by NF-KappaB by various stimuli and also plays a crucial role in carcinogenesis. NF-kappaB acts in each of the main phases of cancer development, which are known as initiation, promotion, and progression.

Inhibition of NF-KappaB activation and signaling prevents aging. Genetic and pharmacological inhibition of NF-KappaB signaling prevents age-associated features of accelerated aging rejuvenation of tissue, as well as the restoration of the transcriptional signature corresponding to young age in mice.

NSAIDs Target Molecular Pathways of Acute and Chronic Inflammatory States

Phospholipid nanoparticle compositions of NSAIDs formed from phospholipids can be used in the treatment of chronic inflammatory states. The inhibitory effects of NSAIDS on the inflammatory response and the prevention hold that NSAIDs inhibit COX activity to prevent prostaglandin synthesis. Phospholipid nanoparticle compositions of NSAIDs formed from phospholipids effect NF-kappaB activation in the actions of these agents. NSAIDs inhibit NF-kappaB activation and regulatory activity for a wide range of diseases and conditions in which inflammation plays a critical role. NSAIDs as a drug group suppress NF-kappaB activation through inhibition of IKK activity, leading to suppression of $I^\kappa B_\alpha$ degradation.

NSAIDs Differ in Ability to Suppress Activation of Inflammatory Pathways

Nonsteroidal anti-inflammatory drugs agents differ in their ability to suppress NF-KappaB activation. Eleven different NSAIDs including aspirin, ibuprofen, sulindac, naproxen, indomethacin, diclofenac, celecoxib, and tamoxifen along with dexamethasone and the nutraceuticals resveratrol and curcumin were investigated. All compounds inhibited TNF-induced NF-KappaB activation, but with highly variable efficacy. Naproxen was 6 times more potent than aspirin and 3.5 times more potent than Ibuprofen at NF-kappaB inhibition.

Studies have shown NSAIDs can effectively inhibit NF-kappaB activity at concentrations comparable to those used in therapy. The list includes Aspirin, Ibuprofen and Naproxen. NSAIDs inhibit NF-kappaB activation and NF-kappaB-regulated gene expression for anti-inflammatory and anti-proliferative (anti-cancer development) effects. They inhibited $I^\kappa B_\alpha$ kinase and suppress $I^\kappa B_\alpha$ degradation and NF-$^\kappa$B-regulated reporter gene expression. They also suppress NF-$^\kappa$B-regulated COX-2 and cyclin D1 protein expression in a dose-dependent manner. NSAID suppress NF-$^\kappa$B activation through inhibition of IKK activity, leading to suppression of $I^\kappa B_\alpha$ degradation.

Aspirin and sodium salicylate are examples of NSAIDs for which the molecular target is, at least in part, NF-KappaB. At concentrations measured in the serum of patients treated with these agents for chronic inflammatory conditions, both aspirin and salicylate inhibit activation of the NF-KappaB pathway.

NSAID Therapy in Inflammatory Disorders

Extensive research has shown that classical NSAIDs have a potential both in prevention and treatment of a wide variety of inflammatory disorders that include cancer, arthritis, cardiovascular diseases, atherosclerosis, depression cognitive decline and Alzheimer's disease. For example, long-term use of NSAID therapy reduces the risk of developing Alzheimer's disease and delays the onset of the disease and suppressed both the inflammation and pathology of Alzheimer's disease. Results support NSAID use and reduction in cognitive decline in older persons. This disclosure teaches treatment of inflammatory disorders through the use of phospholipid nanoparticle compositions of NSAIDs formed from phospholipids and simpler lipids.

Research shows the chronic administration of NSAIDs reduced the risk of cancer incidences. Both the epidemiological and animal studies showed an inverse association between the incidence of various cancers and the use of aspirin or other NSAIDs. Results showed a significant exponential decline in the risk with increasing intake of NSAIDs (primarily aspirin or ibuprofen) for 7-10 malignancies including the four major types: colon, breast, lung, and prostate cancer. Daily intake of NSAIDs, primarily aspirin, produced risk reductions of 63% for colon, 39% for breast, 36% for lung, and 39% for prostate cancer. Significant risk reductions were also observed for esophageal (73%), stomach (62%), and ovarian cancer (47%). Sulindac is a non-steroidal anti-inflammatory agent that is structurally related to indomethacin. Sulindac is a non-steroidal anti-inflammatory agent that is related both structurally and pharmacologically to indomethacin. In addition to its anti-inflammatory properties, sulindac has been demonstrated to have a role in the prevention of colon cancer. This disclosure teaches a reduced risk of transfer incidence providing the treatment of inflammatory disorders through the use of phospholipid nanoparticle compositions of NSAIDs formed from phospholipids and simpler lipids.

NSAID Therapy as Aging Intervention

A growing body of evidence shows non-steroidal anti-inflammatory drugs (NSAIDs) that target NF-kappaB activation and related inflammatory pathways have clinical significance for the prevention and treatment of aging pathologies diseases related to chronic low-grade inflammation. Numerous research papers have recommended the regular use of NSAIDS in aging intervention In a 2013 paper published in the journal Nature Communications, the team describes how inflammation triggers senescence of cells and as a potential driver of accelerated aging and how we might be able to delay it. NSAIDs therapy including treatment with ibuprofen, could reverse the progression of cell senescence and restore the ability of tissues to regenerate This disclosure teaches treatment of inflammatory disorders through the use of phospholipid nanoparticle compositions of NSAIDs formed from phospholipids and simpler lipids; wherein stomach damages can be avoided. These damages include but are not limited to Induced joint inflammation, GI bleeding and formation of GI adhesions or perforations. A double blind clinical study involving 125 patients studied the effect of ibuprofen pre-associated with phosphatidylcholine (ibuprofen/PC) found application of ibuprofen/PC reduces the side effects while providing the same effectiveness, particularly in older patients. In a pilot double blind, crossover study on Aspirin—phosphatidylcholine complex of 93% purity produced significantly fewer gastric lesions in human subjects than unmodified aspirin over a 4-day period.

Low Solubility, Dissolution and Bioavailability of NSAIDs

The oral absorption of a given NSAID and any drug for that matter depends on the balance of its solubility in the aqueous environment of the gastrointestinal lumen and its capability to diffuse across the lipophilic apical membrane of enterocytes. Generally, drugs must dissolve in order to be absorbed and achieve sufficient bioavailability. The bioavailability (the percentage of the drug absorbed compared to its initial dosage) is limited by this insolubility. Poorly water soluble drugs often require high doses in order to reach therapeutic plasma concentrations after oral administration. Dissolution rate is a function of the surface area of the particles and solubility. The surface area can be determined through the control of the particle size. Therefore, the bioavailability of the water insoluble drugs can be improved by reduction in their particle size (increase in surface area).

The poor solubility and low dissolution rate of poorly water-soluble drugs in the aqueous gastrointestinal fluids often result in low and insufficient bioavailability. This is the case for NSAIDS. NSAIDs as a drug class exhibit low solubility that creates low bioavailability. The solubility water at 25° C. for Salicylic acid, Ibuprofen, Naproxen and Ketoprofen are 3, 21, 15.9 and 0.5 mg/ml. Relative to compounds with higher aqueous solubility, poorly soluble NSAIDs compounds in tablet forms may exhibit incomplete release from the dosage form in the gut necessary for absorption.

| Solubility of NSAIDs at 25 C.* | |
|---|---|
| Acetylsalicylic acid | 3.3 mg/ml |
| Salicylic acid, | 3 mg/ml |
| Ibuprofen | 21 mg ml |
| Naproxen | 15.9 mg/ml |
| Ketoprofen | 51 mg/ml |
| Indomethacin | .937 mg/ml |
| Diclofenac, | 50 mg/ml |

*http://www.drugbank.ca

Solubility and Dissolution Improvement of NSAIDs with Nanoparticles

Solubility and dissolution improvement of the NSAID Aceclofenac using different nanocarriers compared to water was tested. The increase solubility of aceclofenac formulated into a solid lipid nanoparticle (stearic acid Poloxamer-188 sodium taurocholate and ethanol), a polymeric nanosuspension (PLGA, Pluroinc, 168, acetone) and nanoemulsions (Labrafil, Triacetin, Tween-80, Transcutol-P, compared to its solubility in distilled water at 25° C. was 6948 5582 and 1325 folds.

Oral lipid nanocarriers of the NSAID Ibuprofen of composed of MCTs, essential phospholipids (lipidS75); Solutol and Cremaphor were formed by phase inversion. Oral administration of nanocarriers Ibuprofen showed an 18% increase of AUC and a 27% higher mean residence time. The antinociceptive (pain relief) effect was similar for oral Ibuprofen administration, drug solutions, and lipid nanocarriers at 30 min after administration. Pain relief was prolonged up to 4 h in the lipid nanocarrier group.

Toxicity of Polymer Carriers of NSAIDs

Nanoparticle and microspheres and polymer carriers of NSAIDs formed from biodegradable, non-biodegradable, natural and synthetic polymers have been investigated. They have been reported to increase NSAIDs bioavailability, accumulate in the inflamed areas, reduce the NSAIDs GI toxic effects and sustain NSAID activity. These polymeric carriers consist of a monolithic spherical structure with the drug or therapeutic agent distributed throughout a polymer matrix either as a molecular dispersion or as a dispersion of particles.

Polymer carrier structures include a wide range of surfactants, emulsifiers and excipients in their molecular compositions. Polymer nanoparticles are recognized to contain toxic monomers and solvents that form toxic degradation products. From the past studies of polymeric nanoparticles exhibiting cytotoxic effects, the safety profile of current polymer carriers of NSAIDs is not encouraging or not reported extensively so as to conclude that they are a safe carrier for NSAIDs. By contrast, the cytotoxicity of lipid nanoparticles can be minimal or absent, due to their better physiological acceptability when compared to polymeric nanoparticles.

Safety Considerations of NSAID Nanoparticles

At the nanoscale, the physical and chemical properties of materials differ in fundamental ways from the properties of the atoms and molecules of bulk materials. These effects occur because reduced particle size exponentially increasing the surface area for biological interactions and increased ability of the nanoparticle to cross biological membranes and excipients to alter metabolism. The various combinations of polymers, surfactants, emulsifiers and excipients used the different techniques described in the literature for producing nanostructured carriers of NSAIDs can produce adverse effects, including toxicity and inflammation. There is inadequate testing of many of these ingredients for safety in nanocarriers and these techniques of manufacturing nanoparticles to conclude they are safe for commercial drug applications.

Phospholipid nanoparticles can be manufactured with biocompatible, physiological and GRAS structural materials and excipients that degrade quickly into non-toxic compounds that are easily eliminated through physiologic metabolic pathways and endogenous enzymes. The lipid matrix degradation occurs mostly by lipases whereas only non-enzymatic hydrolytic processes degrade a minor part. Lipid carriers prepared with several lipids and emulsifying agents have shown low toxicity in humans.

The toxicity of the surfactants used in producing in lipid nanoparticles has been explored. Surfactants are important excipients frequently used in nanoparticulate systems as stabilizers and solulibilizers. There are many commercially available surfactants. They have different properties and the same surfactant may have a wide range of applications. Studies found the pharmaceutical surfactants lecithin;

phophshadylchine fractions, poloxamer, sodium cholate and polysorbate 80 were well tolerated and non-toxic in nanoparticles. They were shown unlikely to induce allergic reactions, hypersensitivity or cytokine production.

Even lipid nanoparticles may not be innocuous. Cytotoxicity of lipid nanoparticles can occur due to the inclusion of unsafe components such as non-ionic emulsifiers and harmful preservatives. The method of manufacturing a lipid nanoparticle can risk contamination. Methods like solvent evaporation and emulsification; emulsification-solvent diffusion technique and micro emulsion technique can produce nanoparticles with toxic solvent residues left over from product production or high levels of surfactants and other excipients that cause toxicity.

Production techniques of phospholipid nanoparticle comprising milling, homogenation and ultrasonic processing that use biocompatible, physiological and GRAS excipients have produced lipid nanoparticle structures showing minimal toxicity.

Intraoral Sublingual Delivery of Nanoparticle NSAIDs

The absorption of the drugs like NSAIDs through the sublingual route is 3 to 10 times greater than the oral route and is only surpassed by hypodermic injection. Sublingual administration of an NSAID avoids contact with the GI tract and causing gastrointestinal problems and NSAID pathogenic effects. Sublingual administration of an NSAID can relieve pain faster than oral administration because this route avoids barrier functions of the GI tract and the first passage of the drug in the liver where some of the drug is metabolized.

Patients received piroxicam, administered orally or sublingually, after undergoing removal of symmetrically positioned lower third molars, no significant differences in pain scores were observed between the routes of delivery used in this study. A randomized, controlled, parallel-group trial in patients who had undergone orthopedic operations found. Piroxicam sublingual tablets relieved post-operative pain faster than piroxicam regular tablet. Both formulations showed a statistically significant reduction (p<0.001) in pain, tenderness and inflammation as compared with baseline values. A Double-blind, placebo-controlled, randomized clinical trial of sublingual or intramuscular piroxicam in the treatment of renal colic found sublingual to be as effective as the IM injection.

Transdermal Delivery of Nanoparticle NSAIDs

In transdermal administration, the NSAIDs have to pass the stratum corneum layer to reach lower layers of the skin and/or to enter systemic circulation. Several formulation approaches for cutaneous administration of NSAIDs have been used and tested. Furthermore, studies have been conducted on novel drug delivery systems for transdermal administration of NSAID into systemic circulation and to target different layers of the skin include crystals, nano/micro emulsions, liposomes, solid lipid particles and patches. The conventional pharmaceutical forms are gels, creams and ointments.

Studies conducted with the transdermal administration of different NSAIDS in lipid nanocarriers and nanoemulsions have shown increase in NSAIDs permeation with respect to its conventional solution and prolonged in vivo anti-inflammatory activity increase in bioavailability as compared to oral tablet formulations. The absorption of aceclofenac by transdermal applied nanoemulsions and nanoemulsion gel resulted in 2.95 and 2.60-fold increase in bioavailability as compared to oral tablet formulation. Results of these studies indicated that the nanoemulsions can be successfully used as potential vehicle for enhancement of bioavailability of aceclofenac.

Ocular Delivery of Nanoparticle NSAIDS

Inflammation plays a major role in eye disease and degenerative eye conditions Activation of the NF-kappaB inflammatory pathway in ocular cells plays an important role in ocular disorders including its involvement in chemical injury, ultraviolet (UV) radiation-induced injury, eye infections, allergic eye diseases, dry eye, pterygium, and corneal graft rejection. Anti-inflammatory NSAIDs and other drugs have been used in the treatment of these ocular conditions. The inflammatory pro staglandins and activation of the NF-kappaB pathway plays a role in the pathogenesis of degenerative eye conditions like diabetic retinopathy and age-related macular degeneration. NSAIDs that work these metabolic pathways have shown therapeutic activity in treating these disorders and other inflammatory disorders of the eye.

Ocular drug transport barriers pose a challenge for NSAID drug delivery comprising the ocular surface epithelium, the tear film and internal barriers of the blood-aqueous and blood-retina barriers. Ocular drug delivery efficiency depends on the barriers and the clearance from the choroidal, conjunctival vessels and lymphatic. Traditional drug administration reduces the clinical efficacy especially for poor water-soluble NSAID molecules and for the posterior segment of the eye. Lipid and polymer nanoparticles eye drops have been designed to overcome these barriers to increase the drug penetration at the target site and prolong the drug levels by few internals of drug administrations in lower doses without any toxicity compared to the conventional preparations. Lipid nanoparticle eye drops are especially useful in ocular drug delivery because they have enhanced the corneal absorption of drugs, improve the ocular bioavailability of both hydrophilic and lipophilic drugs and do not show biotoxicity since they are prepared from physiological lipids.

Intranasal Delivery of Nanoparticle NSAIDs

Transmucosal routes of drug delivery via mucosal linings of the nasal as well as ocular and oral cavity show distinct advantages over peroral administration for systemic drug delivery. Compared to other biological membranes, the nasal mucosa is a rather porous and thin endothelial basal membrane. It also has a rapid blood flow, with a highly vascularized epithelial layer and a vast absorption area with microvilli in epithelial cells. The passage of drugs across the nasal mucosa occurs in three ways: paracellular, transcellular or transcytotic.

The proven advantages for intranasal delivery of NSAIDs include bypassing first pass effect, avoiding presystemic metabolism, eliminating NSAIDs GI pathogenic effects, achieving rapid systemic therapeutic blood levels, increasing NSAID bioavailability, increasing bioactivity and increasing the therapeutic index. Intranasal delivery has clinical benefits like reduction in drug dosage and systemic exposure, which results in lesser side effects In some cases, absorption of almost the whole dose can be achieved and the pharmacokinetics can be similar to intravenous administration. Furthermore, intranasal delivery enables NSAIDs that do not cross the BBB to be delivered to the central nervous system in a few minutes along with both the olfactory and trigeminal neuronal pathway.

Among the major disadvantages of the nasal route is the limited volume of application, the difficulty of high molecular weight drugs to pass through the nasal mucosa, the presence of pathological conditions, mucocilliary drug clearance, enzymatic barriers and irritation of the nasal mucosa.

There is potential for irritation and damage to the phospholipid nasal mucosa and ciliary action from the long-term use of of NSAIDs administered as conventional nasal spray and drops. Nasal absorption of salicylic acid was decreased with increasing concentration of administered drug and low absorption of high concentration of salicylic acid was lined with its nasal epithelial toxicity and nasal membrane resistance.

Nasal absorption is particularly low for hydrophilic drugs like NSAIDs and drugs with low solubility and dissolution in aqueous solutions. Absorption is also low with aqueous solutions that have a low retention time on the mucosal membrane's surface for absorption. Among the most promising strategies recently developed to improve the nasal bioavailability of drugs are lipid and polymer nanoparticle systems and intranasal gels. Studies have shown lipid and polymer nanoparticle drug carriers and administration as nasal gels increase drug absorption and retention for greater bioavailability and therapeutic effects.

Oil-in-water emulsion compositions for the intranasal administration of drugs, including NSAIDs such as meloxicam, are described in WO 15 00/24373. Although such compositions are useful for the delivery of poorly water-soluble drugs in a liquid form and may offer improved nasal tolerance of irritant drugs, emulsions are complex systems and present a number of stability and manufacturing challenges.

NSAID Transport into the Central Nervous System

NSAIDs show only limited accessibility distribution across the blood-brain barrier to the central nervous system (CNS) at normal doses and produce significant gastrointestinal toxicity. Clinical studies demonstrated minimal concentrations of traditional, nonselective NSAIDs, such as indomethacin, ibuprofen, ketoprofen, piroprofen, in CSF. Researchers found brain levels of naproxen about 1% of that in plasma after oral dosing in rats at concentrations that produce neuroprotective actions in cell culture studies. The limited accessibility of NSAIDs into the CNS and brain may impede or limit potential neuroprotective actions of NSAIDs require higher doses to achieve neuroprotective effects and can predispose an individual to serious GI toxicity.

The CNS therapeutic index for neuroprotection and treatment of disease may be enhanced by improved brain delivery. Smaller sized lipid nanoparticle drug delivery carriers that mimic lipoproteins have been described as means for delivering lipophilic drugs (that includes NSAIDs) from the systemic circulation across the BBB into the CNS and brain. Thus enabling their targeting of inflammation in the CNS, providing neuroprotection and treatment of inflammatory-related neurodegenerative conditions.

Similar lipid nanoparticle drug delivery carrier compositions are recognized for direct nose-to-brain drug delivery via the intranasal route of administration. The highest concentration of particles delivered through the nose ends up in the olfactory bulb, medulla, and brainstem at the entry point of the trigeminal nerves. However, widespread delivery to the striatum and cortex also occurs. The intranasal route of delivery provides a noninvasive way to bypass the blood-brain barrier and avoid issues of systemic toxicity.

NSAID Transport into the Central Nervous System

NSAIDs show only limited accessibility distribution across the blood-brain barrier to the central nervous system (CNS) at normal doses and produce significant gastrointestinal toxicity. Clinical studies demonstrated minimal concentrations of traditional, nonselective NSAIDs, such as indomethacin, ibuprofen, ketoprofen, piroprofen, in CSF. Researchers found brain levels of naproxen about 1% of that in plasma after oral dosing in rats at concentrations that produce neuroprotective actions in cell culture studies. The limited accessibility of NSAIDs into the CNS and brain may impede or limit potential neuroprotective actions of NSAIDs require higher doses to achieve neuroprotective effects and can predispose an individual to serious GI toxicity.

The CNS therapeutic index for neuroprotection and treatment of disease may be enhanced by improved brain delivery. Smaller sized lipid nanoparticle drug delivery carriers that mimic lipoproteins have been described as means for delivering lipophilic drugs (that includes NSAIDs) from the systemic circulation across the BBB into the CNS and brain. Thus enabling their targeting of inflammation in the CNS, providing neuroprotection and treatment of inflammatory-related neurodegenerative conditions.

Similar lipid nanoparticle drug delivery carrier compositions are recognized for direct nose-to-brain drug delivery via the intranasal route of administration. The highest concentration of particles delivered through the nose ends up in the olfactory bulb, medulla, and brainstem at the entry point of the trigeminal nerves. However, widespread delivery to the striatum and cortex also occurs. The intranasal route of delivery provides a noninvasive way to bypass the blood-brain barrier and avoid issues of systemic toxicity.

Anti-Inflammatory Cannabidiol

Cannabidiol, the most abundant nonpsychoactive constituent of *Cannabis sativa*, has been shown to exert anti-inflammatory effects both in vitro and in various preclinical models of neurodegeneration and inflammatory disorders, independent from classical CB1 and CB2 receptors. Cannabidiol is shown to attenuate NF-Kappa B activation and pro-inflammatory cytokines and mediators that include TNF-αlpha and inducible NO synthase, iNOS.

Cannabidiol has a tremendous therapeutic potential in the treatment of a wide range inflammatory disorders. A major impediment to the clinical application of Cannabidiol is low oral bioavailability of 13-19% and insolubility in water.

General Compositions

This disclosure relates to phospholipid nanoparticle compositions of NSAIDs formed from phospholipids and simpler lipids in an unfired sequential process that encapsulate a high concentration of an NSAIDs; increase NSAID transport across hydrophobic mucosa; increase the bioavailability of the NSAID 2-fold to 10-fold, decrease the dose of NSAIDs 2-fold to 10-fold less than an amount of NSAID needed to illicit similar therapeutic effects compared to currently available OTC and prescription NSAID pills and capsules, where the phospholipid nanoparticle structure reduce or eliminate pathogenic effects of NSAIDs and enable daily, long-term efficacious NSAID therapy, and treatment and prevention of inflammatory disorders and global inflammation.

The present disclosure also relates phospholipid NSAID compositions for treating fever, inflamed tissues, platelet aggregation, and/or central and/or peripheral or nervous system disorders; and/or preventing thrombosis; and in a therapeutic dose 2-fold to 10-fold less than typical dose of currently sold NSAID pills and capsules; and without causing NSAID pathogenic effects.

The disclosure provides phospholipid nanoparticle carrier compositions of NSAIDS with increased bioavailability, therapeutic activity and therapeutic index to prevent, treat and/or ameliorate age-related and non-age related inflammatory disorders and global inflammation.

The disclosure provides phospholipid nanoparticle carrier compositions of anti-inflammatory nutraceuticals including resveratrol, cinnamaldehyde, green tea polyphenols, lipoic acid, and curcuminoids with increased bioavailability, therapeutic activity and therapeutic index to prevent, treat and/or ameliorate age-related and non-age related inflammatory disorders and global inflammation.

The disclosure provides phospholipid nanoparticle carrier compositions of anti-inflammatory Cannabidiol with increased bioavailability, therapeutic activity and therapeutic index to prevent, treat and/or ameliorate age-related and non-age related inflammatory disorders and global inflammation.

The disclosure provides phospholipid nanoparticle carrier compositions of NSAIDS with increased bioavailability, therapeutic activity and therapeutic index to block activation of the NF-kappaB inflammatory signaling pathways, inflammatory cytokines and mediators of inflammation.

The disclosure provides methods of delivering phospholipid nanoparticle carrier compositions of NSAIDS as NanoSphere liquids gels for effective NSAID therapy and circumvent the problems of current OTC and prescription NSAIDs tablets and capsules low solubility, dissolution and bioavailability; and the problems people have in swallowing pills and capsules.

The disclosure provides phospholipid nanoparticle carrier compositions of NSAIDS formed with essential phospholipids and methods of delivery that reduce or eliminate NSAID pathogenic effects including GI ulceration, bleeding, liver damage, kidney damage, and/or cardiovascular side-effects, and increase NSAID therapeutic activity and for NSAID Therapy and treating inflammatory disorders and global inflammation.

The disclosure provides phospholipid nanoparticle carrier compositions of NSAIDS where the nanoparticle carrier reduces pathogenic or toxic effects of the NSAIDs and increase NSAID bioavailability and/or therapeutic activity for NSAID Therapy—preventing, treating and or ameliorating inflammatory disorders and global inflammation.

The disclosure provides phospholipid nanoparticle carrier compositions of NSAIDS where the nanoparticle carriers' constituents include the essential phospholipid phosphatidylcholine and method of delivery that reduce or eliminate the pathogenic or toxic effects of the NSAIDs; and increase NSAID bioavailability and therapeutic activity for NSAID therapy—preventing, treating and or ameliorating inflammatory disorders and global inflammation.

The disclosure provides phospholipid nanoparticle carrier compositions of NSAIDS and methods of delivery where the nanoparticle carrier or constituents act to reduce or eliminate the pathogenic effects of the NSAID and increase NSAID bioavailability, therapeutic activity and therapeutic index for long term and safe NSAID Therapy.

The disclosure provides phospholipid nanoparticle carrier compositions of NSAIDS for delivery into the systemic circulation across the GI tract mucosal barrier, and where the nanoparticle carrier and phospholipid constituents act to reduce or eliminate pathogenic effects of the NSAIDs, and increase NSAIDs bioavailability and therapeutic activity for NSAID therapy—preventing, treating and or ameliorating inflammatory disorders and global inflammation.

The disclosure provides phospholipid nanoparticle carrier compositions of NSAIDS for administration and delivery into the systemic circulation across the sublingual or buccal oral mucosal barrier and to prevent NSAID GI toxicity and where the nanoparticle carriers increase NSAIDs bioavailability and therapeutic activity for NSAID therapy—preventing, treating and or ameliorating inflammatory disorders and global inflammation.

The disclosure provides phospholipid nanoparticle carrier compositions of NSAIDS for administration and delivery into the systemic circulation across the epidermal and dermal barriers and to prevent NSAID GI toxicity and where the nanoparticle carriers increase NSAIDs bioavailability and therapeutic activity for NSAID therapy—preventing, treating and or ameliorating inflammatory disorders and global inflammation.

The disclosure provides phospholipid nanoparticle carrier compositions of NSAIDS for administration and delivery into the systemic circulation across the epidermal and dermal barriers and to prevent NSAID GI pathogenic effects and where the nanoparticle carriers increase NSAIDs bioavailability and therapeutic activity for NSAID therapy—preventing, treating and or ameliorating inflammatory disorders and global inflammation.

The disclosure provides phospholipid nanoparticle carrier compositions of NSAIDS administration and delivery into the systemic circulation across the mucosa barrier of the nasal cavity, and prevent NSAID GI t pathogenic effects and where the nanoparticle carrier increase NSAIDs bioavailability and therapeutic activity for NSAID therapy—preventing, treating and or ameliorating inflammatory disorders and global inflammation.

The disclosure provides phospholipid nanoparticle carrier compositions of NSAIDS and methods of administration and delivery that carry NSAIDs across the BBB, into the central nervous system, the brain and neural tissue; and increase NSAIDs bioavailability and therapeutic activity for NSAID therapy —preventing, treating and or ameliorating neural inflammatory disorders and global inflammation.

The disclosure teaches the increased dose-fraction of delivered NSAIDs across the BBB into the brain and neural tissue and into the central nervous system for NSAID therapy in a phospholipid nanoparticle carrier composition when compared to the delivery of regular NSAID across the BBB.

General Methods for Making the General Compositions

The disclosure teaches a process for producing phospholipid lipid structural nanoparticle carrier compositions of NSAIDS that are formed from an essential phospholipid (phosphatidylcholine) and a simple lipid.

The disclosure teaches a process for producing phospholipid lipid structural nanoparticle carrier compositions of NSAIDS that are formed from phospholipids and a simple lipid.

The disclosure teaches a process for producing phospholipid lipid nanoparticle carrier compositions of NSAIDS where the production method is free of polymers.

The disclosure teaches a process for producing phospholipid lipid nanoparticle carrier compositions of NSAIDS where the production method is free of surfactants.

The disclosure teaches a process for producing phospholipid lipid nanoparticle carrier compositions of NSAIDS where the production method is free of surfactants, solvents and/or expedients that cause toxicity, inflammation and adverse effects as nanoparticles.

The disclosure teaches a process for producing phospholipid lipid structural nanoparticle carrier composition that provides a composition including a high concentration of an NSAID) systems comprising a production method incorporating nanoparticle production schemes. This phospholipid lipid nanoparticle carrier system is used for the delivery of NSAIDs into mammals.

The disclosure teaches a process for producing phospholipid lipid nanoparticle carrier compositions of NSAIDS where the production method comprises a combination of milling, homogenation and ultrasonic processing in sequence. using cold techniques in each step. At least one NSAID is incorporated into the process, effective for administration to mammals.

The disclosure teaches a nanoparticle method of assembly wherein the assembly comprises three assembly techniques in a sequential unified process without the use of heat, without polymers that encapsulate NSAIDs with biocompatible non-toxic biocompatible essential phospholipids, simpler lipids and solvents that are FDA approved and safe as nanoparticles.

The disclosure teaches a nanoparticle method of assembly wherein the assembly comprises three assembly techniques in a sequential unified process without the use of heat, without polymers that encapsulate NSAIDs with biocompatible non-toxic biocompatible essential phospholipids, simple lipids, surfactants, solvents and excipients that are FDA approved and safe as nanoparticles.

The disclosure teaches a process for producing phospholipid lipid nanoparticle carrier compositions of anti-inflammatory nutraceuticals where the production method is free of surfactants, solvents and/or expedients that cause toxicity, inflammation and adverse effects as nanoparticles.

The disclosure teaches a process for producing phospholipid lipid structural nanoparticle carrier composition that provides a composition including a high concentration anti-inflammatory nutraceuticals comprising a production method incorporating nanoparticle production schemes. This phospholipid lipid nanoparticle carrier system is used for the delivery of anti-inflammatory nutraceuticals into mammals.

The disclosure teaches a process for producing phospholipid lipid nanoparticle carrier compositions of anti-inflammatory nutraceuticals where the production method comprises a combination of milling, homogenation and ultrasonic processing in sequence. using cold techniques in each step. At least one nutraceutical is incorporated into the process, effective for administration to mammals.

The disclosure teaches a nanoparticle method of assembly wherein the assembly comprises three assembly techniques in a sequential unified process without the use of heat, without polymers that encapsulate anti-inflammatory nutraceuticals with biocompatible non-toxic biocompatible essential phospholipids, simpler lipids and solvents that are FDA approved and safe as nanoparticles.

The disclosure teaches a process for producing phospholipid lipid nanoparticle carrier compositions of anti-inflammatory Cannabidiol where the production method is free of surfactants, solvents and/or expedients that cause toxicity, inflammation and adverse effects as nanoparticles.

The disclosure teaches a process for producing phospholipid lipid structural nanoparticle carrier composition that provides a composition including a high concentration of anti-inflammatory Cannabidiol comprising a production method incorporating nanoparticle production schemes. This phospholipid lipid nanoparticle carrier system is used for the delivery of anti-inflammatory Cannabidiol into mammals.

The disclosure teaches a process for producing phospholipid lipid nanoparticle carrier compositions of anti-inflammatory Cannabidiol where the production method comprises a combination of milling, homogenation and ultrasonic processing in sequence. using cold techniques in each step, and is effective for administration to mammals.

The disclosure teaches a nanoparticle method of assembly wherein the assembly comprises three assembly techniques in a sequential unified process without the use of heat, without polymers that encapsulate anti-inflammatory Cannabidiol with biocompatible non-toxic biocompatible essential phospholipids, simpler lipids and solvents that are FDA approved and safe as nanoparticles.

The disclosure teaches a nanoparticle method of assembly wherein the assembly comprises three assembly techniques in a sequential unified process without the use of heat, without polymers that encapsulate anti-inflammatory Cannabidiol with biocompatible non-toxic biocompatible essential phospholipids, simple lipids, surfactants, solvents and excipients that are FDA approved and safe as nanoparticles.

In one embodiment, the disclosure teaches a method of assembly for nanosphere compositional structures wherein the method of assembly efficiently encapsulates NSAIDs into a stable phospholipid nanoparticle structure with a particle size distribution from 50 to 150 nm. This method of assembly allows for commercial production.

The disclosure teaches a nanoparticle method of assembly wherein the assembly comprises three nanoparticle assembly techniques in a sequential unified process encapsulating NSAIDs. The nanoparticles are stable phospholipid nanoparticle compositional structures with a particle size distribution from about 50 to 150 nm. The assembly can be scaled for commercial production and scalable to commercially available size production.

The disclosure further teaches the products for administration via the sublingual mucosa and buccal mucosa of a mammal. The disclosure further teaches a product, by the process disclosed above, for administration across ocular barriers and to ocular tissues. The disclosure further teaches a product, by the process disclosed above, for transdermal administration across dermal and epidermal barriers. The disclosure further teaches a product, by the process disclosed above, for administration across the blood brain barriers (BBB). The disclosure further teaches a product, by the process disclosed above, for administration across the gastrointestinal (GI) tract mucosal barrier. The disclosure further teaches a product, by the process disclosed above, for administration across the nasal mucosal barrier.

The disclosure further teaches a method for producing a NSAID for delivery via the sublingual mucosa and buccal mucosa of a mammal. The disclosure further teaches a method for producing a NSAID for administration across ocular barriers and to ocular tissues of a mammal. The disclosure further teaches a method for producing a NSAID for administration across dermal and epidermal barriers. The disclosure further teaches a method for producing a NSAID for administration across the BBB. The disclosure further teaches a method for producing a NSAID for administration across the GI tract mucosal barrier. The disclosure further teaches a method for producing a NSAID for administration across the nasal mucosal barrier.

The disclosure further teaches a method for producing a NSAID for delivery via the sublingual mucosa and buccal mucosa of a mammal for NSAID therapy and the reduction or elimination of NSAID pathogenic effects. The disclosure further teaches a method for producing a NSAID for administration across ocular barriers and to ocular tissues of a mammal for NSAID therapy and the reduction or elimination of NSAID pathogenic effects. The disclosure further teaches a method for producing a NSAID for administration across dermal and epidermal barriers for NSAID therapy and the reduction or elimination of NSAID pathogenic effects. The disclosure further teaches a method for producing a NSAID for administration across the BBB for NSAID therapy and the reduction or elimination of NSAID pathogenic effects. The disclosure further teaches a method for producing a NSAID for administration across the GI tract mucosal barrier for NSAID therapy and the reduction or elimination of NSAID pathogenic effects. The disclosure further teaches a method for producing a NSAID for administration across the nasal mucosal barrier for NSAID therapy and the reduction or elimination of NSAID pathogenic effects.

The disclosure further teaches a method for encapsulating a NSAID into a phospholipid nanoparticle for delivery into the systemic circulation via the sublingual mucosa and buccal mucosa of a mammal for NSAID therapy.

The disclosure further teaches a method for encapsulating a NSAID into a phospholipid nanoparticle composition, for delivery into the systemic circulation across the GI tract mucosal barrier for NSAID therapy.

The disclosure further teaches a method for encapsulating a NSAID into a phospholipid nanoparticle composition for delivery across dermal and epidermal barriers into the systemic circulation for NSAID therapy.

The disclosure further teaches a method for encapsulating a NSAID into a phospholipid nanoparticle for delivery across the mucosa barrier of the nasal cavity into the systemic circulation for NSAID therapy.

The disclosure further teaches a method for encapsulating a NSAID into a phospholipid nanoparticle composition for delivery across ocular barriers and into to ocular tissues for NSAID therapy.

The disclosure further teaches a method for encapsulating a NSAID into a phospholipid nanoparticle across the blood-brain barrier and into the central and peripheral nervous system for NSAID therapy.

The disclosure teaches formulating phospholipid lipid nanoparticles containing NSAIDs into solid dose forms including dissolvable tablets, granules lozenges, pellets, and other forms for intraoral delivery by sublingual and buccal administration. Suitable formulation methods include spray drying of lyophilization of lipid structured nanoparticle dispersions with suitable excipients followed by incorporation of a dry powder into a tablet, or pellet. Another method is granulating phospholipid nanoparticles liquid dispersions with excipients and binders into powders for compression into tablets or pellets for sublingual and buccal delivery. Phospholipid nanoparticles may be incorporated into lozenges, lollipops, gum, gels and films for intra-oral delivery.

The disclosure teaches a method of forming phospholipid lipid nanoparticles comprising of at least one of the following NSAIDs Propionic acid drugs such as Fenoprofen calcium (Nalfon®), Flurbiprofen (Ansaid®), Suprofen. Benoxaprofen, Ibuprofen (prescription Motrin®), Ibuprofen (200 mg. over the counter Nuprin, Motrin 1B®), Ketoprofen (Orduis, Oruvall®), Naproxen (Naprosyn®), Naproxen sodium (Aleve, Anaprox, Aflaxen®), Oxaprozin (Daypro®), or the like; Acetic acid drug such as Diclofenac sodium (Voltaren®), Diclofenac potassium (Cataflam®), Etodolac (Lodine®), Indomethacin (Indocin®), Ketorolac tromethamine (Acular, Toradol® intramuscular), Ketorolac (oral Toradol®), or the like; Ketone drugs such as Nabumetone (Relafen®), Sulindac (Clinoril®), Tolmetin sodium (Tolectin®), or the like; Fenamate drugs such as Meclofenamate sodium (Meclomen®), Mefenamic acid (Ponstel®), or the like; Oxicam drugs such as Piroxicam (Dolibid®), or the like; Salicylic acid drugs such as Diflunisal (Feldene®), Aspirin, or the like; Pyrazolin acid drugs such as Oxyphenbutazone (Tandearil®), Phenylbutazone (Butazolidin®), or COX-2 inhibitors such as celecoxib, meloxicam, diclofenac, meloxicam, piroxicam, Celebrex, Vioxx, or the like: or mixtures or combinations thereof.

Phospholipid Nanoparticle Compositions of NSAIDs

Since many lipids and phospholipids are part of living constituents, they are considered to be suitable biomaterials to form phospholipid nanoparticle carriers. Many suitable lipids are available that have been used to form lipid nanoparticle carriers that are GRAS listed, biocompatable and entirely non-toxic to humans. Synthetic and natural polymers offer an almost infinite array of chemical composition and structure combinations. However, only a few have the requirements that make them useful as nanoparticle factor carriers. Many polymers have toxic properties and can produce side effects in humans and most have not been tested as nanoparticles to recommend them safe for human use in NSAID therapy and treating inflammatory disorders.

As a result, the preferred type of nanoparticle carrier that is best suited overall for use as nanoparticle carriers of NSAIDs in NSAID therapy and treating inflammatory disorders in this disclosure are the phospholipid-structured nanoparticles.

The preferred phospholipid nanoparticles for use in this disclosure for encapsulating NSAISs include solid lipid nanoparticles, lipid emulsion nanoparticles and NanoSpheres. They are known to provide the highest degree of biocompatibility controlled release, efficient targeting, stability and high therapeutic index to their NSAID payload.

"Solid lipid nanoparticles" essentially have a solid form. These dynamic structures are synthesized from natural biocompatible lipids, phospholipids and excipients and contain an encapsulated inner core phase. They provide controlled release, efficient targeting, and stability to its cargo or payload.

"Lipid emulsion nanoparticles" are dynamic structured, dispersed particle droplets created from natural lipids that possess an outer phospholipid layer and an encapsulated inner lipid core.

"NanoSpheres" are dynamically structured liquid gels synthesized from natural biocompatible simple lipids, essential phospholipids and other excipients Phospholipid nanoparticles of this disclosure are constructed from phospholipids and simpler lipids. Phospholipid is the same material that comprises the major components of biological membranes and lipoproteins. As biological membranes, they exist as either sphingolipids or phosphodiglycerides. The most abundant essential phospholipid is phosphatidylcholine, also known as lecithin. A highly purified essential phospholipid phosphatidylcholine fraction of greater than 85% phosphatidylcholine is the preferred phospholipid in forming of these phospholipid nanoparticles in this disclosure.

The phospholipids in the process of synthesizing the phospholipid nanoparticle compositions encapsulating NSAIDs in this disclosure include phosphatidycholine, phosphatidylethanolamine, phosphatidylglycerol, phosphatidylserine, phosphatidylinositol, cardiolipin, and the derivatives of these phospholipids. Preferred phospholipids in lipid nanoparticles of this disclosure should be biocompatible, GRAS listed and non-toxic as nanoparticles.

Suitable commercially available natural phospholipids from soya lecithin fractionation for this disclosure include Lipoid Phospholipon 80, 80 N, 80 H 85 G, 90 G, 90 H and 100 H; and Lipoid's solubilized lecithin liquid carrier systems that include Phosal 35 B. 50 SA, 53 MCT and 75 SA.

The simpler lipids in the process of synthesizing the lipid structured nanoparticle compositions in this disclosure may include fatty acids, triglycerides triacylglycerols, acylglycerols, waxes, cholesterol, sphingolipids, and the derivatives of these lipids. The preferred simpler lipids in this disclosure are medium chained triglycerides, safflower oil and sesame oil. Preferred simpler lipids used in forming phospholipid nanoparticles of this disclosure should biocompatible, GRAS listed and non-toxic as nanoparticles.

The preferred of weight/volume ratios of phospholipids to simpler lipids in forming phospholipid nanoparticles of this disclosure is from 4:1 to 1:4. Preferably, the weight ratio is from about 2:1 to about 1:2.

The preferred percentage of weight/volume ratios of NSAIDs to phospholipid nanoparticle structural materials (phospholipids+simpler lipids) in forming phospholipid nanoparticles of this disclosure is from 4:1 to 1:5. Preferably, the weight ratio is from about 3:1 to about 1:2.

The assembly of the phospholipid nanoparticle compositions of NSAIDs in this disclosure may include surfactants and suitable emulsifiers such lecithins, polysorbates, monoglycerides, diglycerides, triglycerides, glyceryl monoleate, polysorbates and polaxamers that are known to the art. Surfactants and suitable emulsifiers should be selected that do not induce adverse changes in barrier functions, do not induce toxic and allergic effects, do not induce adverse effects to the nanoparticles, and do not induce adverse effects to the transported NSAIDs. Preferred surfactants and emulsifiers in nanoparticles of this disclosure should be biocompatible, GRAS listed and non-toxic as nanoparticles.

Phospholipid nanoparticle assemblies of NSAIDs in this disclosure may be dispersed in a solvent and carrier fluid during formulation. Suitable carrier fluids and solvents include water, sterile saline, glycerides glycerine, ethanol, sorbitol, lipids, fatty acids, glycine, and silicone oils. Suitable carrier fluids should be GRAS listed, biocompatible and non-toxic as nanoparticles.

The assembly of the phospholipid nanoparticle compositions in this disclosure may include preservatives selected according to the route of delivery, barrier function, properties of nanoparticle materials, and properties of the encapsulated NSAIDS. Plus, preservatives should be selected that do not induce changes in barrier functions, do not induce toxic and allergic effects, do not induce adverse effects to the nanoparticles, and do not induce adverse effects to the transported NSAIDs. Some of the preservatives for consideration in use include tocopherols, ascorbyl palmitate, sorbates, parabens, optiphen, thimersal, benzoic acid, benzalkonium chloride, benzehtkonium chloride polyquaternium-1, ethyl lauroyl arginate, and rosemary oleoresin, Jeecide and Optiphen.

The preferred preservatives in this disclosure are tocopherols, ascorbyl palmitate and sorbates for intraoral and peroral administered formulations; benzalkonium chloride, benzehtkonium chloride for ocular and intranasal administered formulations; and sorbates, Jeecide and Optiphen for transdermal administered formulations. Preferred preservatives in phospholipid nanoparticles of this disclosure should be biocompatible, GRAS listed and non-toxic as nanoparticles. Preferred preservatives should not interfere with the delivery of the NSAIDs.

Nanoparticle size is extremely important to the biological properties and functioning of the nanoparticle carriers of this disclosure. Nanoparticles with diameters ranging from 20 nm to 200 nm demonstrate the most prolonged circulation times. Smaller nanoparticle sizes and a lipid structured nanoparticle composition can facilitate easier passage across cell membranes, enhancing cellular uptake and greater delivery NSAIDs to intracellular targets and inflamed tissues.

The assembly of phospholipid nanoparticle compositions in the present disclosure may include sweeteners for intraoral and peroral routes of delivery to enhance acceptability to the consumer. The sweeteners used may be natural sweeteners or artificial sweeteners. Natural sweeteners include Stevia extract Steviol Glycosides, xylitol, sucrose, fructose, fructooligosaccharides, glucose, glucose syrup, invert sugar, maltodextrins, Magnasweet, eryritol, sorbitol, maltitol, lactitol, mannitol, and isomalt. Examples of artificial sweeteners include sucralose, aspartame, acesulfame K, neohesperidine, dihydrochalcone, thaumatin, saccharin and saccharin salts. Preferred sweeteners for this disclosure should be sucralose, cesulfame K and natural sweeteners such such as steviol glycosides, xylitol, erythritol and thaumatin. Magnasweet.

Typically the sweetener content will be about 0.05 to 2.5% w/w. Preferred sweeteners in nanoparticles of this disclosure should be biocompatible, GRAS listed and non-toxic as nanoparticles.

The assembly of phospholipid nanoparticle compositions in the present disclosure may include flavors for intraoral and peroral routes of delivery to enhance acceptability to the consumer. The flavors used may be natural sweeteners or artificial sweeteners. Examples of flavoring agents useful in the compositions of the invention include fruit (e.g. pineapple or citrus) concentrates and concentrated aqueous or non-aqueous flavors such as flavor oils. Typically the sweetener content will be about 0.1 to 1% w/w. Preferred flavors in phospholipid nanoparticles of this disclosure should be biocompatible, GRAS listed and non-toxic as nanoparticles.

A smaller nanoparticle size and a natural lipid and phospholipid nanoparticle composition (that mimics a plasma lipoprotein), can avoid extensive presystemic metabolism, avoid uptake by the reticuloendothelial system of the liver and spleen as a foreign substance, and prevent premature clearance from the body, is the preferred nanoparticle composition in this disclosure.

This disclosure teaches phospholipid nanoparticle compositions of NSAIDs with proven benefits over conventional OTC and prescription pill and capsules that include:
  a) Increased NSAID bioavailability through transmucosal absorption and direct oral-cavity delivery;
  b) Increased NSAID bioavailability, bioactivity and therapeutic index for NSAID therapy
  c) Sustained blood levels for longer-lasting beneficial actions;
  d) Higher-potency responses, allowing reductions in amount and frequency of administration;
  e) Transport of NSAIDs across the BBB and into the central nervous system for therapeutic activity
  f) Improved user convenience (less frequent use and easier compliance;
  g) Increased circulatory half-life. Improved kinetics and dynamics, such as decreased enzyme degradation, prevention of hepatic metabolism to inactive byproducts, reduced renal clearance, and fewer adverse reactions;
  h) Site-specific anti-inflammatory actions that minimize loss of biological activity and expand therapeutic potential;
  i) Unique molecular "stealth technology," cloaking from the mononuclear phagocytic system and enzymatic destruction, thus prolonging and increasing the beneficial effects;

j) Reduction or elimination of NSAID pathogenic effects;
k) No requirement to swallow pills and capsules;
l) And improved cost-effectiveness on a per-unit amount.

This disclosure relates to the significant increase of phospholipid nanoparticles compositions to carry NSAIDs across mucosa barriers into the systemic circulation, past the BBB, into the central nervous system, into ocular cells, into tissues and into target cells; and increase the bioavailability, bioactivity and efficacy of NSAIDs for therapeutic activity in NSAID therapy, treating inflammatory disorders and global inflammation. The increased bioavailability and bioactivity of NSAIDs for NSAID therapy can range from a 2-fold increase to a 10-fold increase. The actual increase amount depends on the molecular characteristics of the NSAID, the encapsulation characteristics into phospholipid nanoparticles, the structural characteristic of the phospholipid nanoparticles, the method and vehicles of administration and metabolic difference between users.

The increased bioactivity produced by a phospholipid nanoparticle NSAID composition does not result in an increase in toxicity and pathogenic acclivity of the NSAID, but an increased therapeutic index as evidenced by the data present herein.

Each NSAID has a different dose range per tablet and different recommended amounts when taken orally. The typical range of doses for the NSAIDs sold in the United State are:

| Generic name | Usual dose of NSAID Tablets & Capsules |
| --- | --- |
| Celecoxib | 100-200 mg day −1 |
| Aspirin | 2.6-6 g day 4-5 divided doses |
| Celecoxib | 100-200 mg day −1 |
| Diclofenac | 50 mg BID |
| Diflunisal | 0.25-0.75 g BID |
| Etodolac | 200-300 mg BID-QID |
| Fenoprofen | 300-600 mg QID |
| Flurbiprofen | 100 mg BID-TID |
| Ibuprofen | 200-800 mg QID |
| Indomethacin | 25-50 mg TID-QID |
| Ketoprofen | 75 mg TID |
| Meclofenamate | 50-100 mg TID-QID |
| Mefenamic acid | 250 mg QID |
| Meloxicam | 7.5-15 mg OD |
| Nabumetone | 500 mg BID |
| Naproxen | 250-500 mg BID |
| Oxaprozin | 600 mg OD |
| Piroxicam | 10-20 mg OD |
| Sulindac | 150-200 mg BID |
| Tolmetin | 400-600 mg TID |

The increase in bioactivity and bioactivity of NSAIDs produced by a phospholipid nanoparticle NSAID composition of this disclosure results in dose reduction to produce equivalent therapeutic actions compared to the standard doses of commercial NSAID tablets and capsules to illicit a given therapeutic effect response. The dose reduction can range from a 2-fold reduction in mg dose to a 10-fold reduction in mg dose. Preferably, the range is from about a 2-fold reduction to about a 10 fold reduction in mg NSAID dose.

The dosage of a phospholipid nanoparticle NSAID composition is from about 10% to about 90% of the recommended dose needed to treat a specific condition The decrease in NSAID dosages from a phospholipid nanoparticle NSAID composition of this disclosure, increases the occurrence of NSAID pathogenic effects, increases the therapeutic index and has other tangible benefits that include increased patient compliance, increased cost effectiveness and no requirement to swallow pills and capsules.

The process of synthesizing lipid nanoparticles in the present disclosure may include homogenization techniques such as hot high pressure homogenization technique, cold high pressure homogenization technique, melt emulsification ultrasound (ultrasonication) homogenization technique, high shear homogenization and/or ultrasound technique, microemulsion technique, emulsification-solvent evaporation technique, solvent displacement or injection technique, emulsification-solvent diffusion technique, phase inversion technique, film ultrasonication dispersion technique, and multiple emulsion technique.

The disclosure teaches a method for manufacture of lipid nanoparticles a combination of three techniques, sequentially performed for dispersion comprising milling (physical grinding), homogenation (high speed stirring emulsification) and ultrasonic processing (high wattage flow through ultrasound sonification). These techniques can be performed in this sequential order or may be performed sequentially in alternate orders.

Administration of NSAIDS in Phospholipid Nanoparticles by Different Methods

Oral therapy of NSAIDs is proven effective, but the clinical use is often limited because of their GI toxicity and causing adverse effects such as irritation and ulceration of the gastro-intestinal mucosa. This disclosure of administration of NSAIDs encapsulated in phospholipid lipid nanospheres significantly reduces or eliminates the problems of NSAIDs pathogenic effects from the orally administered conventional NSAIDs tablets and capsules; and maintains relatively consistent plasma levels for long term NSAID therapy, treating inflammatory disorders and treating global inflammation.

This disclosure of administration of NSAIDs encapsulated in phospholipid NanoSpheres via the intraoral, intranasal or transdermal methods bypasses contact with the epithelium of gastrointestinal tract and the problems of GI toxicity of the oral route of administration of conventional NSAIDs tablets and capsules and maintains relatively consistent plasma levels for long-term NSAID therapy, treating inflammatory disorders and treating global inflammation.

The Phospholipid Nanoparticle carrier compositions of NSAIDs in this disclosure can be designed for all possible routes of administration, generally improving both bioavailability and bioactivity of the carried NSAID. They represent an alternative class of vehicles to liposomes, emulsions, aqueous solutions and solid formed tablets and capsules to transport NSAIDs to target cells and tissues for NSAID therapy, treating inflammatory disorders and treating global inflammation.

Intraoral Transport of Phospholipid Nanoparticle NSAIDs Compositions Across the Oral Mucosa The disclosure teaches methods of administering phospholipid nanoparticle carrier compositions of NSAIDs to the sublingual mucosa and buccal mucosa of the oral cavity to increase the delivery, absorption and the bioavailability of NSAIDs into the blood stream and target cells and tissues of mammals.

The disclosure teaches intraoral sublingual or buccal delivery of phospholipid nanoparticle carrier compositions of NSAIDs to increase the NSAIDs bioavailability, bioactivity, therapeutic activity and therapeutic index in NSAID therapy.

The disclosure teaches intraoral sublingual or buccal delivery of phospholipid nanoparticle carrier compositions of NSAIDs to reduce NSAID pathogenic effects by avoiding direct contact with the GI tract and the inclusion of essential phospholipids the nanoparticle's structural composition to eliminate or reduce pathogenic effects of NSAIDs and increase their therapeutic index.

The disclosure teaches the intraoral sublingual or buccal delivery of phospholipid nanoparticle carrier compositions of NSAIDs for the safe and long term use of NSAIDs and in NSAID Therapy, and/or treating inflammatory disorders and/or treating global inflammation.

Another aspect of this disclosure relates to the increased dose-fraction of intraoral delivered nanosized NSAIDs across the intraoral mucosa into the systemic circulation for NSAID therapy and treating inflammatory disorders in a phospholipid nanoparticle carrier composition when compared to oral delivery of the currently available NSAIDs capsules and tablets through the GI tract into the systemic circulation.

Peroral Transport of Phospholipid Nanoparticle NSAIDs Compositions Across the GI Mucosa The disclosure teaches methods of the oral administration of phospholipid nanoparticle carrier compositions of NSAIDs across the mucosal membrane barriers of the GI tract to increase the delivery, absorption and the bioavailability of NSAIDs into the blood stream and target cells and tissues of mammals.

The disclosure teaches oral administration of phospholipid nanoparticle carrier composition of NSAIDs across the mucosal membrane barriers of the GI tract to increase the NSAIDs bioavailability, bioactivity, therapeutic activity and therapeutic index in NSAID therapy.

The disclosure teaches the oral administration of phospholipid nanoparticle carrier composition of NSAIDs across the mucosal membrane barriers of the GI tract to increase the NSAIDs bioavailability, therapeutic activity and/or potency in reducing inflammation and preventing, treating and/or ameliorating inflammatory disorders.

The disclosure teaches the oral administration of phospholipid nanoparticle carrier composition of NSAIDs across the mucosal membrane barriers of the GI tract to reduce NSAID pathogenic effects by incorporating essential phospholipids in the nanoparticle's structural composition.

The disclosure teaches the oral administration of phospholipid nanoparticle carrier composition of NSAIDs across the mucosal membrane barriers of the GI tract for the safe and long term use of NSAIDs and in NSAID Therapy.

Another aspect of this disclosure relates to increased dose-fraction of oral delivered nanosized NSAIDs across mucosal membrane barriers of the GI tract into the systemic circulation for NSAID therapy and treating inflammatory disorders in a phospholipid nanoparticle carrier composition when compared to oral delivery of the currently available NSAIDs capsules and tablets through the GI tract into the systemic circulation.

Transdermal Transport of Phospholipid Nanoparticle NSAIDs Compositions Across the Dermis The disclosure teaches methods of transdermal administration of phospholipid nanoparticle carrier compositions of NSAIDs across the epidermis and dermis to increase the delivery, absorption and the bioavailability of NSAIDs into the blood stream and target cells and tissues of mammals.

The disclosure teaches transdermal administration of phospholipid nanoparticle carrier composition of NSAIDs across the epidermis and dermis to increase the NSAIDs bioavailability, bioactivity, therapeutic activity and therapeutic index in NSAID therapy.

The disclosure teaches transdermal administration of phospholipid nanoparticle carrier composition of NSAIDs across the epidermis and dermis to increase the NSAIDs bioavailability, therapeutic activity and/or potency in reducing inflammation and preventing, treating and/or ameliorating inflammatory disorders.

The disclosure teaches the transdermal administration of phospholipid nanoparticle carrier composition of NSAIDs across the epidermis and dermis to reduce NSAID pathogenic effects by avoiding direct contact with the GI tract and the inclusion of essential phospholipids the nanoparticle's structural composition to reduce the pathogenic effects of NSAIDs.

Another aspect of this disclosure relates to the increased dose-fraction of transdermal delivered nanosized NSAIDs across epidermal and dermal barriers into the systemic circulation for NSAID therapy and treating inflammatory disorders in a phospholipid nanoparticle carrier composition when compared to oral delivery of the currently available NSAIDs capsules and tablets through the GI tract into the systemic circulation.

The disclosure teaches the transdermal administration of phospholipid nanoparticle carrier composition of NSAIDs across epidermal and dermal barriers for the safe and long use of NSAIDs and in NSAID Therapy, and/or treating inflammatory disorders and/or treating global inflammation.

The disclosure teaches a phospholipid nanoparticle liquid gel carrier composition of NSAIDs with advantages compared with other external skin preparations, such as creams and liniments. The phospholipid nanoparticle liquid gels of this disclosure provide more adjustable parameters in their preparation, and in treatments offer the advantages of enhancing the NSAIDs bioavailability for therapeutic activity therapeutic and lowering or elimination side effects. Other advantages include Protection of the NSAIDs from deactivation (chemical, enzymatic or immunological);

Increases the specificity of action and efficacy at cellular and/or molecular level.

Increased average life span

Lacking in toxicity, they are biodegradable and can be prepared industrially on a large scale.

Intranasal Transport of Phospholipid Nanoparticle NSAIDs Compositions Across the Nasal Cavity The disclosure teaches methods of the intranasal administration of phospholipid nanoparticle carrier compositions of NSAIDs across the membranes of the nasal cavity to increase the delivery, absorption and the bioavailability of NSAIDs into the blood stream and target cells and tissues of mammals.

The disclosure teaches intranasal administration of phospholipid nanoparticle carrier composition of NSAIDs across the membranes of the nasal cavity to increase the NSAIDs bioavailability; and/or the NSAIDs therapeutic activity and/or NSAIDs potencies in NSAID therapy.

The disclosure teaches intranasal administration of phospholipid nanoparticle carrier composition of NSAIDs across the membranes of the nasal cavity to increase the NSAIDs bioavailability, bioactivity, therapeutic activity and therapeutic index in NSAID therapy.

The disclosure teaches the transdermal administration of phospholipid nanoparticle carrier composition of NSAIDs across membranes of the nasal cavity to reduce NSAID pathogenic effects by avoiding direct contact with the GI tract and the inclusion of essential phospholipids the nanoparticle's structural composition to reduce or eliminate pathogenic effects of NSAIDs.

The disclosure teaches the intranasal administration of phospholipid nanoparticle carrier composition of NSAIDs across membranes of the nasal cavity for the safe and long-term use of NSAIDs and in NSAID Therapy, and/or treating inflammatory disorders and/or treating global inflammation.

Another aspect of this disclosure relates to increased dose-fraction of intranasal delivered nanosized NSAIDs across membranes of the nasal cavity into the systemic circulation for NSAID therapy and treating inflammatory disorders in a phospholipid nanoparticle carrier composition when compared to oral delivery of the currently available NSAIDs capsules and tablets through the GI tract into the systemic circulation.

The compositions of the invention may be administered to the nasal cavity in any suitable form, for example in the form of drops or a spray. The preferred method is a NanoSphere liquid gel. Methods suitable for administering a composition to the nasal cavity will be well known by the person of ordinary skill in the art. Any suitable method may be used. The preferred method of administration is the use of a spray device.

Transport of Phospholipid Nanoparticle NSAIDs Compositions Across Ocular Barriers The disclosure teaches methods of the ocular administration of phospholipid nanoparticle carrier compositions of NSAIDs across ocular surface epithelium, the tear film and internal barriers of the blood-aqueous and blood-retina barriers to increase the delivery, absorption and the bioavailability of NSAIDs The disclosure teaches methods for ocular administration of phospholipid nanoparticle carrier compositions of NSAIDs across the membranes across ocular surface epithelium, the tear film and internal barriers of the blood-aqueous and blood-retina barrier to increase the NSAIDs bioavailability, bioactivity, therapeutic activity and therapeutic index in ocular NSAID therapy for treating ocular inflammation, inflammatory disorders and/or pain.

The disclosure teaches methods for ocular administration of phospholipid nanoparticle carrier compositions of NSAIDs to increase the NSAIDs penetration at the target sites and prolong the drug's levels.

The disclosure teaches the ocular administration of phospholipid nanoparticle carrier compositions of NSAIDs to increase the NSAIDs bioavailability, bioactivity, therapeutic activity and therapeutic index in ocular NSAID therapy.

Phospholipid Nanoparticle NSAIDs Compositions for Introral Delivery Transport Across the Oral Mucosa The disclosure further teaches a method of administering and delivering lipid structured nanoparticles containing NSAIDs to the oral mucosa for transport into the systemic circulation by employing an intraoral phospholipid nanoparticle delivery system composition.

This disclosure teaches NanoSphere phospholipid nanoparticle compositions that are taken by sublingual administration. The liquid nanosphere gel is administered under the tongue for transport directly into the blood stream. Sublingual drug solutes are rapidly absorbed into the reticulated vein, which lies underneath the oral mucosa, and transported through the facial veins, internal jugular vein, and bra ciocephalic vein and then drained in to systemic circulation.

This disclosure teaches methods of intraoral administration of phospholipid nanoparticle compositions with advantages over the swallowing of conventional OTC and prescription NSAIDs:

The absorption of the drug through the sublingual route is 3 to 10 times greater than the oral route and is only surpassed by hypodermic injection;

Sublingual administration of an NSAID can relieve pain faster than oral administration because this route avoids barrier functions of the GI tract and the first passage of the drug in the liver where some of the drug is metabolized;

Sublingual administration of NSAIDs[18] may relieve pain faster than oral administration because the drug is absorbed by the veins in the floor of the mouth, leading directly to the superior vena cava, thus resulting in faster distribution of the drug to all tissues through the bloodstream. Drugs administered circulate through the bloodstream via the inferior vena cava, which takes longer to distribute the drug to all tissues compared with sublingual administration;

And orally administered NSAIDs pass through the caustic environment of the gastrointestinal tract can produce gastric irritation, not dissolve and/or go into solution for complete absorption, undergo presystemic metabolism and be eliminated intact in the urine. Sublingual administration avoids the gastrointestinal tract.

EXAMPLES

Basic Intraoral NSAID Phospholipid Nanoparticle Carrier Composition Formulation
25-75% —NSAIDs
20-75% —Phospholipids (Lipoid Phospholipon 90 G, Lipoid Phospholipon 90 H, Lipoid Phospholipon 85 G, Lipoid S 75, Lipoid S 40, Lipoid S 80, Lipoid E 80, Lipoid Phosal 75 SA Lipoid, Lipoid Phosal 50 SA, Lipoid Phosal 53 MCT)
25-75% —Simpler Lipids (safflower oil, sunflower oil, medium chain triglycerides)
0-18% —Surfactants (polysorbate 80, polaxamer)
–0-10% —buffers (Sodium hydroxide)
20-60% —Solvents and Carrier Fluids (distilled water, glycerides, lipids)
0-5% —Preservatives (ascorbyl palmitate, rosemary oleoresin, tocopherol, potassium sorbate)

Basic Peroral NSAID Phospholipid Nanoparticle Carrier Composition Formulation
25-75% —NSAIDs
20-75% —Phospholipids (Lipoid Phospholipon 90 G, Lipoid Phospholipon 90 H, Lipoid Phospholipon 85 G, Lipoid S 75, Lipoid S 40, Lipoid S 80, Lipoid E 80, Lipoid Phosal 75 SA Lipoid, Lipoid Phosal 50 SA, Lipoid Phosal 53 MCT)
25-75% —Simpler Lipids (Medium Chain Triglycerides Safflower Seed Oil, etc.)
0-20% —Surfactants (polysorbate 80, polxamer)
–0-10% —buffers (Sodium hydroxide)
20-60% —Solvents and Carrier Fluids (distilled water, glycerdies, and lipids)
0-5% —Preservatives (ascorbyl palmitate, rosemary oleoresin, tocopherol, potassium sorbate)

Basic NSAID Transdermal Nanoparticle Carrier Composition in a Topical Gel Formulation:
5-25% —NSAIDs
5-20% —Phospholipids (Lipoid Phospholipon 90 G, Lipoid Phospholipon 90 H, Lipoid Phospholipon 85 G, Lipoid S 75, Lipoid E 80, Lipoid Phosal 75 SA Lipoid, Phosal 50 SA, Lipoid Phosal 53 MCT)
5-20% —Simpler Lipids (Medium Chain Triglycerides Safflower Seed Oil, etc.)
5-50% —Penetration Enhancer (Ethanol)
0-10% —Surfactants (Polysorbate 80, Pluronic F68)
1-3% —Gelling Agent (Xanthum Gum, Carbopol)

0.1-1% —Preservatives (Optiphen, Jeecide Potassium Sorbate)

q.s. —Carrier (distilled water)

Basic Ocular NSAID Phospholipid Nanoparticle Carrier Composition in an Ophthalmic Solution Formulation:

5-25% —NSAIDs 5-25% —Phospholipids (Lipoid Phospholipon 90 G, Lipoid Phospholipon 90 H, Lipoid Phospholipon 85 G, Lipoid S 75, Lipoid E 80, etc.)

2-10% —Simpler Lipids (Medium Chain Triglycerides Safflower Seed Oil, etc.)

0-10% —Surfactants (Polysorbate 80, Poxamer)

0.1-0.6% —Moisturizeres (Hydroxypropyl Methylcellulose, Hydroxymethylcellulose, Carboxymethylcellulose, Glycerin)

0.8-1.2% Buffers (Boric Acid, Sodium Borate, etc)

0.8-1.6% Osmolarirty Adjuster (Sodium Chloride, Potassium Chloride, Magnesium Chloride, Zinc Chloride, etc.)

0-5% Preservatives (Polyquaternium-1, benzalkonium chloride)

Basic NSAID Intransal Nanoparticle Carrier Composition 5-25% —NSAIDs 5-25% —Phospholipids (Lipoid Phospholipon 90 G, Lipoid Phospholipon 90 H, Lipoid Phospholipon 85 G, Lipoid S 75, Lipoid E 80, etc.)

2-10% —Simpler Lipids (Medium Chain Triglycerides Safflower Seed Oil, etc.)

5-25% Surfactants (Polaxamer188 Polysorbate 80)

0.5-2.5% —Buffers (monobasic potassium phosphate, dibasic potassium phosphate)

0.6-1.8% —Tonicity Adjustor (Sodium chloride)

0-0.25% —Chelating Agents (EDTA)

0.01-0.05% —Preservatives (Benzalkonium chloride)

q.s. —Carrier (distilled water, lipids)

Example

Procedure for a Naproxen NSAID Phospholipid Nanoparticle Non-Aqueous Carrier Composition for Intraoral Delivery Completely dissolve 2000 mg of phospholipids (Lipoid Phospholipon 85 G) into 3780 mg of medium chain triglycerides (Miglyol 810 N) in a vessel under low heat and stirring at low RPM. Next, discharge 4000 mg of USP Naproxen into the blend. In sequence, pre-nanoparticle blend is ground through a product mill for particle size reduction, homegentated at 10,000 RPM for 10 minutes with an Ultra-Turrax homogenizer under cooling, and processed in an ultrasonifiation system for 35 minutes with 3000 watts of power in a flow through chamber under cooling to form the phospholipid nanoparticle Naproxen composition. Next, 20 mg of potassium sorbate preservative, 150 mg of flavor oil and 50 mg of steviol glycoside sweetener is thoroughly dispersed into the composition.

The weight concentration of Naproxen in the phospholipid nanoparticle Naproxen carrier composition is 40%. Composition is administered to the sublingual mucosa by precision liquid pump device bottle that delivers 125 mcl per pump each dose contains 60 mg of Naproxen phospholipid nanoparticle delivered intra-orally into the systemic circulation with increased bioavailability, therapeutic activity and therapeutic index.

Example

Procedure for a Naproxen NSAID Phospholipid Nanoparticle Aqueous Carrier Composition for Intraoral Delivery.

Completely dissolve 2000 mg of phospholipids (Lipoid Phospholipon 85 G) into in a vessel under low heat and stirring at low RPM containing a blend of 750 mg of polysorbate 80 and 625 mg of medium chain triglycerides (Miglyol 810 N).

Completely dissolve 2000 mg of phospholipids (Lipoid Phospholipon 85 G) into in a vessel under low heat and stirring at 1250 RPM. Next, of 4000 mg USP Naproxen is discharged into the blend. In sequence, pre-nanoparticle blend is ground through a product mill for particle size reduction, homegentated at 10,000 RPM for 10 minutes with an Ultra-Turrax homogenizer under cooling, and processed in an ultrasonifiation system for 35 minutes with 3000 watts of power in a flow through chamber under cooling to form the phospholipid nanoparticle Naproxen composition. Next, 20 mg of potassium sorbate preservative, 150 mg of flavor and 50 mg of xylitol sweetener is thoroughly dispersed into the composition.

The weight concentration of Naproxen in the phospholipid nanoparticle Naproxen carrier composition is 40%. Composition is administered to the sublingual mucosa by precision liquid pump device bottle that delivers 125 mcl per pump. Each dose contains 60 mg of Naproxen phospholipid nanoparticles delivered intra-orally into the systemic circulation with increased bioavailability, therapeutic activity and therapeutic index.

Example

Procedure for an Ibuprofen NSAID Phospholipid Nanoparticle Non-Aqueous Carrier Composition for Peroral Delivery.

Completely dissolved 2500 mg of phospholipids (Lipoid Phospholipon 85 G) is into in a vessel under low heat and stirring at 1250 RPM containing a blend of 750 mg of 4745 mg of medium chain triglycerides (Miglyol 810 N) Next, 5000 mg of USP Naproxen is discharged into the blend. In sequence, pre-nanoparticle blend is ground through a product mill for particle size reduction, homegentated at 10,000 RPM for 10 minutes with an Ultra-Turrax homogenizer under cooling, and processed in an ultrasonifiation system for 35 minutes with 3000 watts of power in a flow through chamber under cooling to form the phospholipid nanoparticle Naproxen composition. Next, 25 mg of potassium sorbate preservative, 165 mg of flavor oil and 63 mg of *Stevia* extract sweetener is thoroughly dispersed into the composition.

The weight concentration of Naproxen in the phospholipid nanoparticle Naproxen carrier composition is 40%. Composition is packaged into 500 mg soft gel capsules or 500 mg unit dose pouches for swallowing. Each capsule and pouch contains a 200 mg dose of Ibuprofen phospholipid nanoparticles delivered through the GI tract into the systemic circulation with increased bioavailability, therapeutic activity and therapeutic index Example Procedure for a Ketoprofen NSAID Phospholipid Nanoparticle Gel Composition for Transdermal Delivery.

Completely dissolve 2595 of phospholipids (Lipoid Phospholipon 85 G, 3355 mg of Kertprofen, 1450 mg of Sunflower seed oil and 1635 mg of polysorbate 80 is into a closed vessel containing 6535 mg of ethanol stirring at 1250 RPM. Heat this vessel to 30° C. Next, discharge 900 mg of water heated to 30° C. into the vessel from a separate heated vessel. Stir this vessel containing pre-nanoparticle blend for 5 minutes. In sequence, pre-nanoparticle blend is ground through a product mill for particle size reduction, homegentated at 10,000 RPM for 10 minutes with a Ultra-Turrax homogenizer under cooling, and processed in an ultrasonifiation system for 40 minutes with 3000 watts of power in a flow through chamber under cooling to form the phospholipid nanoparticle Naproxen composition. Discharge 250 mg of Xanthum gum into a vessel containing the blend stirring at 1250 RPM followed by 33 mg of potassium sorbate preservative, and stir for 5 minutes.

The weight concentration of Ketoprofen in the phospholipid nanoparticle carrier composition is 20%. Composition is administered topically to skin in a dispenser that delivers 250 mg of Keoprofen gel per application. Each dose contains 50 mg of Keotprofen phospholipid nanoparticles delivered transdermally into the systemic circulation with increased bioavailability, therapeutic activity and therapeutic index While the apparatus and method have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action, which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the FIGURES was chosen and described in order to best explain the principles of the invention, the practical application, and to enable others of ordinary skill in the art to understand the invention for various embodiments with various modifications as are suited to the particular use contemplated.

The invention claimed is:

1. A method of administering NSAIDS to a mammal, comprising;
   (a) providing a composition formulation comprising nanoparticles comprising NSAIDS, essential phospholipids, fatty acids and solvents, wherein NSAIDs comprise 25-75% of the carrier composition formulation, wherein the essential phospholipids comprise more than 75% of (3-sn-phosphatidyl) choline; and wherein the fatty acids are selected from the group consisting of medium chain triglycerides which are liquid at room temperature, safflower seed oil and sunflower oil, and solvents; wherein the nanoparticles have a particle size distribution from 50 to 150 nm; wherein the nanoparticles do not comprise a polymer, and wherein the NSAIDs are encapsulated in the nanoparticle, and
   (b) administering the composition formulation to a mammal via the sublingual or buccal mucosa.

2. A method of administering NSAIDS to a mammal, comprising;
   (a) providing a composition formulation comprising nanoparticles comprising NSAIDS, essential phospholipids, fatty acids and solvents, wherein NSAIDs comprise 5-25% of the carrier composition formulation, wherein the essential phospholipids comprise more than 75% of (3-sn-phosphatidyl) choline; and wherein the fatty acids are selected from the group consisting of medium chain triglycerides which are liquid at room temperature, safflower seed oil and sunflower oil, and solvents; wherein the nanoparticles have a particle size distribution from 50 to 150 nm; wherein the nanoparticles do not comprise a polymer, and wherein the NSAIDs are encapsulated in the nanoparticle,
   (b) administering the composition formulation to a mammal across ocular barriers into ocular tissues, and
   (c) administering the nanoparticle structure to a mammal directing nose-to-brain drug delivery into CNS via the intranasal route of administration wherein the Blood Brain Barrier is bypassed.

* * * * *